Figure 1:
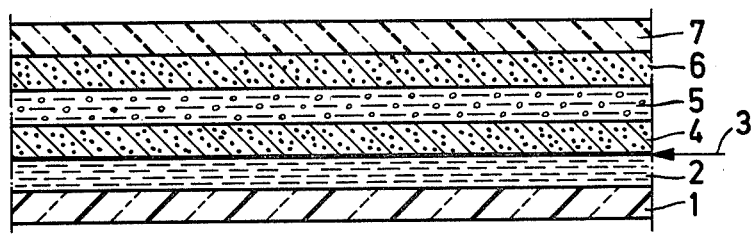

United States Patent [19]

Mason et al.

[11] 4,386,149

[45] May 31, 1983

[54] PROCESS FOR THE PRODUCTION OF PHOTOGRAPHIC IMAGES BY DYE DIFFUSION TRANSFER AND PHOTOGRAPHIC MATERIAL SUITABLE IN THIS PROCESS

[75] Inventors: Leslie F. A. Mason, Brentwood; Rainer Kitzing, Ingatestone; Brian R. D. Whitear, Brentwood; William E. Long, Brentwood; Glenn P. Wood, Brentwood; David L. R. Reeves, Brentwood, all of England

[73] Assignee: Ciba-Geigy AG, Basel, Switzerland

[21] Appl. No.: 235,352

[22] Filed: Feb. 13, 1981

Related U.S. Application Data

[62] Division of Ser. No. 14,776, Feb. 23, 1979, Pat. No. 4,269,928.

[30] Foreign Application Priority Data

| Feb. 28, 1978 [GB] | United Kingdom | 7789/78 |
| Oct. 13, 1978 [GB] | United Kingdom | 40401/78 |
| Oct. 30, 1978 [GB] | United Kingdom | 42414/78 |
| Nov. 20, 1978 [GB] | United Kingdom | 45305/78 |

[51] Int. Cl.³ .............................................. G03C 1/48
[52] U.S. Cl. .................................... 430/213; 430/220; 430/222; 430/223; 430/523; 430/524; 430/559; 430/561
[58] Field of Search ............... 430/213, 220, 222, 223, 430/559, 561, 524, 523

[56] References Cited

U.S. PATENT DOCUMENTS

| 3,227,552 | 1/1966 | Whitmore | 430/226 |
| 3,330,655 | 7/1967 | Salminen | 430/226 |
| 3,585,028 | 6/1971 | Stephens | 430/223 |
| 3,617,275 | 11/1971 | Bloom et al. | 430/223 |
| 3,628,952 | 12/1971 | Puschel et al. | 430/223 |
| 4,168,976 | 9/1979 | Campbell et al. | 430/222 |
| 4,269,928 | 5/1981 | Mason et al. | 430/392 |
| 4,271,254 | 6/1981 | Mason et al. | 430/392 |

FOREIGN PATENT DOCUMENTS 1330755 9/1973 United Kingdom .

*Primary Examiner*—J. Travis Brown
*Attorney, Agent, or Firm*—Joseph G. Kolodny

[57] ABSTRACT

A photographic dye diffusion transfer process is provided which operates by imagwise release of a dye.

The dye diffuses to a receiving layer and is mordanted there to give a dye image. The dyes are released from a compound of the formula D—E—F—BAL by reductive cleavage.

D is a group which contains the residue of diffusible dye, BAL is a ballasting group which renders the compound containing it substantive to the layer in which it is present, D and E being joined by any type of chemical bond and E and F represent a single or double bond system which links D and BAL and which has a reduction potential above −200 mV measured against a standard hydrogen electrode at a pH of less than 3 and which bond can be reductively cleaved at a pH of less than 3 by a reducing agent which is able to act as a pH below 3.

10 Claims, 12 Drawing Figures

PROCESS FOR THE PRODUCTION OF PHOTOGRAPHIC IMAGES BY DYE DIFFUSION TRANSFER AND PHOTOGRAPHIC MATERIAL SUITABLE IN THIS PROCESS

This is a division of application Ser. No. 014,776, filed Feb. 23, 1979, now U.S. Pat. No. 4,269,928.

This invention relates to a process for the production of photographic images by dye diffusion transfer, and to a photographic material containing diffusion-resistant dye-releasing compounds suitable for use in this process.

Ever since the advent of photography silver halide salts have been used as the photosensitive agent and for the most part developed silver has been used as the image although in colour photography final dye images have replaced the silver image. However in a large number of photographic materials the final image is still a silver image, e.g. in X-ray materials, microfilms and in graphic arts films as well as in normal black and white high speed camera films. Recently, however, the price of silver has increased to such an extent that ways have been sought in which silver halide can still be used as the photosensitive agent but in which a final dye image is formed even in the photographic materials listed above. By such means there can either be an almost total recovery of the silver used or at least a great reduction in the amount of silver used.

In one method of colour photography the photosensitive agent is a silver salt and a dye developer is used which develops the silver halide and is immobilised and at the same time in the unexposed areas a dye is released which diffuses out of the photosensitive layers into a receptor layer which can be peeled apart from the photosensitive layer. Thus a final dye image is obtained whilst leaving all the silver in the residual material and therefore recoverable. We have discovered a novel photographic diffusion process in which dyes are liberated imagewise from a precursor from the layer in which they were coated to a receiving layer.

Therefore according to the present invention there is provided a process for the production of a photographic image by use of silver halide material which comprises the steps of (a) imagewise exposing a photographic assembly which comprises at least during the silver halide developing step, in order, optionally a supercoat layer, at least one silver halide emulsion layer, a dye mordant layer and a support base, there being optionally one or more interlayers between each of the said components and there being associated with the silver halide emulsion layer a compound of the general formula

$$D-E-F-BAL \quad (1)$$

where D is a group which contains the residue of a diffusible dye, BAL is a ballasting group, D and E being joined by any type of chemical bond, and E and F represent a single or double bond system which links D and BAL and which has a reduction potential above $-200$ mV measured against a standard hydrogen electrode at a pH of less than 3 and which bond can be reductively cleaved at a pH of less than 3 by a reducing agent which is able to act at a pH below 3, (b) processing the exposed assembly to develop the latent image in the silver halide emulsion layer(s), (c) and simultaneously or subsequently producing an imagewise distribution of a reducing agent in an aqueous acid medium having a pH below 3 and reductively cleaving the E—F bond of the compound of formula (1) thereby liberating a diffusible dye imagewise, (d) allowing or causing the diffusible dye to diffuse to the dye mordant layer (receiving layer), (e) and there to mordant the dye to form a dye image having a peak absorption within the range of 300–800 nm.

D may be joined to E by any type of chemical bond including a covalent and an ionic bond. Formula (1) also includes compounds where two or more D groups are attached to BAL by an E—F linkage. Also included are compounds where two or more BAL groups are attached to D by an E—F linkage.

By associated therewith in connection with the silver halide emulsion and the compound D—E—F—BAL of formula (1) is meant that either the compound of formula (1) is present in the silver halide emulsion layer or is in a separate layer which is close enough to the silver halide emulsion layer to allow imagewise diffusion of a reducing agent between the two layers. Preferably however the compound of formula (1) is present in the silver halide emulsion layer.

The silver halide emulsion used may be either a positive or negative working silver halide emulsion. This silver halide emulsion may be sensitised to visible light in the wavelength range of 400–800 nm, or to ultra-violet, X-ray or other high energy irradiation, or to infra-red radiation.

Examples of suitable classes of dyes for the residue D are phthalocyanines, anthraquinones, azines, including oxazines and thiazines, acridines, triphenylmethanes, indigo dyes, oxonols, pyrylium dyes, azo and azoxy dyes.

According to a particular method of the present invention there is provided a process for the production of a photographic image by use of silver halide material which comprises the steps of (a) imagewise exposing a photographic assembly as defined before, (b) processing the exposed assembly with a black and white silver halide developing solution to develop the latent image in the silver halide emulsion layer(s), (c) processing the assembly in a silver dye bleach solution at a pH below 3 in the presence of a silver dye bleach catalyst thereby causing the silver dye bleach catalyst to be reduced in the silver image areas and becoming a reducing agent, and allowing or causing the reduced catalyst in the silver image areas to cleave the E—F bond of the compound of formula (1) thereby liberating a diffusible dye, (d) allowing or causing the diffusible dye to diffuse to the dye mordant layer, (e) and there to mordant the dye to form a dye image having a peak absorption within the range of 300–800 nm.

This method is hereinafter referred to as Method A.

Reduced silver dye bleach catalysts are reducing agents which are capable of cleaving the compounds of formula (1) as hereinbefore defined.

Preferably in this process the compound of formula (1) is present in the silver halide emulsion layer.

In this method A if a negative working silver halide emulsion is used a negative image will be formed in the receiving layer but conversely if a positive working emulsion is used then a positive image will be formed in the receiving layer.

By 'silver dye bleach catalyst' is meant a compound which is used in the silver dye bleach process to accelerate the bleaching of the bleachable dye image. Certain diazine compounds are particularly suitable. These compounds are reduced by image silver to their reduced form. In their reduced form they are able to bleach certain bleachable dyes and in particular azo dyes. In doing so they are converted to their oxidised form but are reduced again by the image silver. Thus the dye bleach catalyst helps in the imagewise bleaching of the azo dye in the silver dye bleach process.

In method A of the process of the present invention as just set forth the action of the silver dye bleach catalyst is to break down the E—F bond in the compound of formula (1) to liberate the diffusible dye. In doing so it is again converted to its oxidised form but is reduced again by the image silver. Thus the dye bleach catalyst in method A causes the reduction of the compound of formula (1) in conformity with the silver image.

Examples of suitable diazine catalysts are 1,4-diazines such as pyrazine compounds and preferably quinoxaline compounds, above all those which are substituted in the 2-, 3-, 5-, 6-, 7- and/or 8-position by lower alkyl, hydroxy alkyl or alkoxy ($C_1$-$C_4$), especially methyl, hydroxymethyl or methoxy, further by acylated hydroxymethyl groups (—$CH_2$—$SO_3H$) or salts thereof, amino or acylated(acetylated)amino groups, carboxyl, sulfonic acid (salts) ($SO_3H$), benzoyl, acetyl, phenyl, benzyl or pyridyl.

Usable dye bleach catalysts are also described in German Auslegeschriften Nos. 2,010,707, 2,144,298 and 2,144,297, in French Patent Specification 1,489,460 and in U.S. Pat. No. 2,270,118.

The silver dye bleach catalyst may be present initially in the photographic material but preferably it is present in the silver dye bleach solution.

According to another particular method of the present invention there is provided a process for the production of a photographic image by use of silver halide material which comprises the steps of (a) imagewise exposing a photographic assembly as defined above, (b) treating the exposed photographic assembly with an aqueous acid processing bath so as to provide in the silver halide emulsion layer or layers a solution or dispersion of a reducing agent which is an E—F bond cleaving/silver halide developing agent (redev compound) thereby to develop the latent silver image in the silver halide emulsion layer(s), and (c) in the non-latent image areas allowing or causing the E—F bond cleaving/silver halide developing agent to cleave the E—F bond of the compound of formula (1), thereby liberating a diffusible dye, (d) allowing or causing the diffusible dye to diffuse to the dye mordant layer, (e) and there to mordant the dye to form a dye image having a peak absorption within the range of 300-800 nm.

This method is hereinafter referred to as Method B.

Preferably in this method the compound of formula (1) is present in the silver halide emulsion layer.

Reducing agents which can reductively cleave the E—F bond at a pH below 3 (e.g. in the presence of strong mineral acids or sulphamic acid) and which are capable of developing a latent silver image at a pH below 3 are hereinafter referred to as redev compounds. Various classes of redev compounds are known. Perhaps the best known class is the reduced form of certain diazine compounds. Diazine compounds are used in the known silver dye bleach process in which they are used to accelerate greatly the bleaching of the dye in accord with the developed silver areas (U.S. Pat. Nos. 3,963,492, 4,014,698 and 4,056,566). However in method B in the process of the present invention the preferred diazine compounds are those which in the reduced or dihydro form are able to develop a latent silver image and also able to reduce the E—F link.

Examples of suitable diazine catalysts are pyrazine and pyrazine compounds.

The reduced 1,4-diazine compounds are preferably used in the form of aqueous solutions. The solution can also contain a mixture of two or more diazines.

The unreduced diazines can be present in the photographic assembly in suspension or as a solution in a high-boiling solvent. Furthermore, the diazines can be incorporated in capsules in the photographic assembly which can be broken by a change in pressure, temperature or pH, in the light-sensitive layer or in an adjacent layer.

Other diazine compounds are described in German Auslegeschriften Nos. 2,010,707, 2,144,298 and 2,144,297, in French Patent Specification 1,489,460 and in U.S. Pat. No. 2,270,118.

It is known from B.P. No. 1,183,176 that the reduced form of such diazine compounds can act as silver halide developing agents.

Another particularly useful class of redev compounds are salts of metallic ions and complexes of metallic ions with suitable ligands which are capable of acting as silver halide developing agents.

Metallic ions which are capable of acting as developing agents for latent silver images are well known (see for example Photographic Processing Chemistry by L. F. A. Mason, Focal Press, 2nd Edition, 1975, pages 177-180). Such metallic ions are the lower valency state ions of variable valency metals. In general they act at low pHs to preserve their active low valency state.

Metallic ions and complexes of metallic ions with suitable ligands which are capable of acting as developing agents for latent silver images in an aqueous acid solution, are able also to act in an acid solution to break the E—F bond in compounds of formula (1) to liberate the diffusible dye. However they are not silver dye bleach catalysts because after cleaving the E—F bond they become oxidised to their higher valency state but can not be reduced to their lower valency state by metallic silver.

Preferred metallic ions for use as redev compounds in the process of the present invention are chromous that is to say $Cr^{++}$, vanadous that is to say $V^{++}$ and titanous that is to say, $Ti^{+++}$.

There may be present also in the redev solution which comprises such metal ions a ligand, e.g. ethylene diamine tetraacetic acid, which beneficially modifies the redox potential of the metal ions.

Thus in method B of the process of the present invention when the exposed photographic assembly which comprises a silver halide emulsion layer and a compound of formula (1) as hereinbefore defined is treated with a solution or dispersion of the redev compound then in the latent silver image areas of the silver halide emulsion layer the redev compound develops the latent silver image and becomes oxidised and thus inactive both as a silver halide developing agent and as a reducing agent for the compound of formula (1).

However, in the non-latent image areas of the silver halide emulsion layer the redev compound in solution or dispersion, when the compound of formula (1) is present in the silver halide emulsion layer, is able to reduce the compound of formula (1) and liberate the diffusible dye. Alternatively when the compound of formula (1) is present in a layer separate from the silver halide emulsion layer the redev compound in solution or dispersion is able to diffuse through the silver halide emulsion, the compound being unaffected by non-latent image areas of the silver halide. When the redev compound reaches the compound of formula (1) layer it reduces this compound and liberates the diffusible dye. In both cases the diffusible dye diffuses to the receiving layer where it is fixed to form a dye image.

In method B of the process of the present invention when a negative working silver halide emulsion is used a direct positive dye image is obtained whilst if a direct positive emulsion is used a negative image is obtained.

The preferred redev compounds of use in the present invention, that is to say the reduced diazine compounds and the lower valency ions of metallic salts or complexes as hereinbefore defined, both act preferably at a pH about 1.

The solution or dispersion of redev compounds of use in method B of the process of the present invention may be prepared and applied to the photographic assembly in a number of different ways.

For example, if the redev compound used is a reduced diazine compound, this compound may be applied to the photographic assembly as a preformed reduced compound. The methods of forming a reduced derivative of a 1,4-diazine compound are described in British Patent Specification No. 1,183,176.

Alternatively, and this is preferred, the reduced diazine compound is produced during the processing step from a diazine compound or from a N-oxide derived therefrom by use of a reducing agent in layer form in an acid medium, the said reducing agent being a metal which in the electrochemical series of the elements is more reducing than silver and as far as and including lanthanum in the series. Examples of metals which are more reducing than silver include copper, lead, tin, bismuth, iron, nickel, cobalt, cadmium, zinc, manganese, berylium, indium, thallium, gallium, aluminium and lanthanum. This method of processing is described in British Patent Specification No. 1,330,755.

Thus in one such method the redev compound is in an inactive form and a solution or dispersion of this compound is contracted with a substance which renders the compound active (or subjected to electrolysis to convert the inactive form to the active form) just before or whilst the solution or dispersion is applied to the exposed photographic assembly.

For example there may be used a vacuum deposited coated metal strip for example a tin or copper film base strip and there is coated on to this coated strip or on the exposed photographic material a solution or paste which comprises a 1,4-diazine compound in an acid medium. The diazine compound is reduced by the metal and diffuses into the photographic material where the reduced diazine compound in the presence of the acid solution acts as a developing agent for the latent silver image.

In an alternative to this method the photographic assembly comprises either in the supercoat layer or below the supercoat layer but above the bottom-most silver halide layer a compound in layer form which is able to render active a solution or dispersion of an inactive redev compound. Thus in this method in step (b) of method B a solution or dispersion of an inactive redev compound is applied to the exposed photographic assembly and when the inactive compound comes into contact with the activating compound it is rendered active and thus able to develop the latent silver image. A colloidal or fine dispersion of a metal which in the electrochemical series is more electro-negative than silver, up to and including lanthanum, may be used. A colloidal dispersion of tin, indium, gallium, lanthanum or especially zinc or aluminium or alloys which include such metals is useful.

It may also be useful to incorporate metal ion complexing agents in the metal dispersion layer to render the redox potential of the metal system more favourable. Under these circumstances the metal used need not necessarily be more electro-negative than silver.

In a further alternative method the redev compound is present initially in a layer in the photographic assembly in an inactive form and in step (b) of method B a solvent for the compound is applied to the exposed photographic assembly and the thus formed solution of the inactive compound is treated in the assembly to convert the compound to the active form. The redev compound may be treated in the assembly by providing in the assembly as well a substance in layer form which renders active the inactive redev compound. In another method at the same time or just after the solvent is applied in step (b) the photographic assembly is subjected to electrolysis. This converts the redev compound to the active form in the assembly.

Similarly if the redev compound consists of simple or complexed metallic ions in a reduced state these ions may be prepared and applied to the photographic assembly in a number of different ways.

For example ($a_1$) a preformed acid solution of the metallic ions may be used, ($b_1$) the acid solution of the metallic ions may be formed externally to the photographic assembly but as a step in the processing sequence, ($c_1$) the acid solution of the simple or complexed reduced metallic ions may be formed in situ in the photographic assembly during the processing sequence.

Thus in the method ($a_1$) the reduced metal ion may be preformed by known methods, such as electrolytic reduction of a suitable oxidised form of the metal ion, zinc amalgam reduction of a suitable oxidised form or formation of the required metal ion complex by admixture of suitable starting materials in the required oxidation state.

When method ($b_1$) is used a strip (foil) of a second metal or a strip having a fine or colloid dispersion of a second metal coated thereon is used, the second metal having a reduction potential sufficiently negative to achieve reduction of the oxidised form of the metallic ion to the reduced form of the metallic ion. The metal strips are e.g. composed of aluminium, iron, zinc or tin; further of indium or alloys which include such metals. When employed in a fine colloid dispersion the metals are for example zinc, tin, iron, nickel, aluminium or indium; further gallium lanthanum, or alloys containing these metals.

There is coated on to this strip a solution or paste which comprises an oxidised form of the metallic ion in acid solution and the thus coated strip is then applied to the exposed photographic assembly. The oxidised form of the metallic ion is reduced by the second metal and diffuses into the photographic assembly where the reduced form of the metallic ion in the presence of the acid solution acts as a developing agent for the latent silver image.

The paste comprises aluminium, zinc, tin, indium, or gallium or alloys which include such metals.

In case (c₁) there may be present in the photographic assemby a layer which contains a fine or colloid dispersion of a second metal which can reduce oxidised forms of the metallic ions to produce the above form of the ions. Such metals include zinc, tin or indium.

Preferably there is present in the processing solution in method B an anti-foggant for example bromide or iodide ions or 1-phenyl-5-mercapto tetrazole.

It is to be understood that the compounds of formula (1). are all compounds of the same type and a compound which can be used in method A as hereinbefore set forth can also be used in method B as hereinbefore set forth.

It is to be understood that the photographic assembly may comprise more than one silver halide photosensitive system having associated therewith a compound of formula (1).

D is the residue of a diffusible dye which after the compound of formula (1) has been reduced becomes a dye which is diffusible in the photographic assembly during processing. Thus the residue D has no ballasting substituents and preferably comprises at least one solubilising group, for example a sulphonic acid or sulphonate substituent group, a hydroxyl group, amino group, ammonium group, sulphonamide group, carboxylic acid or carboxylate group, phosphoric acid or phosphate group, phosphine group or phosphonium group.

Particularly useful compounds of formula (1) are compounds of the general formula

D—N=N—BAL     (2)

and their corresponding hydrazo compounds of the general formula

D—NH—NH—BAL     (3)

where in formulae (2) and (3) D and BAL have the meanings assigned to them above.

The hydrazo compounds of formula (3) are the dihydro derivatives of the azo compounds of formula (2), thus for ease of reference the term "azo compound" as used hereinafter also covers the derived hydrazo compounds and refers to compounds of formulae (2) and (3).

Therefore according to a particular method of the present invention there is provided a process for the production of a photographic image which comprises imagewise exposing a photographic assembly which comprises a photosensitive system and associated therewith either an azo compound of the general formula

D—N=N—BAL     (2)

or a hydrazo compound of the general formula

D—NH—NH—BAL     (3)

where in formulae (2) and (3) D represents a diffusible dye residue and BAL represents a ballasting group which renders the azo or hydrazo compound substantive to the layer in which it is present, processing the exposed photographic assembly to produce an imagewise distribution of a reducing compound which is capable of reducing the azo or hydrazo compound, causing the reducing compound to reduce imagewise the azo or hydrazo compound, thereby liberating a diffusible dye and causing or allowing the diffusible dye to diffuse imagewise to a receiving layer and there to mordant the dye to form a dye image having a peak absorption within the range of 300–800 nm.

In one special method of the process just defined there is provided a process for the production of a photographic image which comprises (a) imagewise exposing a photographic assembly which comprises at least during the processing steps a silver halide emulsion layer and present in the silver halide emulsion layer or in a layer in operative contact therewith an azo compound as just defined, and a dye receiving layer, (b) developing the latent image in the silver halide emulsion layer with a black and white silver halide developing solution to produce a silver image in the silver halide emulsion layer, (c) processing the assembly in a silver dye bleach solution in the presence of a silver dye bleach catalyst (as hereinbefore defined) thereby causing the catalyst to be reduced in the silver image areas, (d) causing the reduced catalyst either to imagewise reduce the azo compound present in the silver halide emulsion layer or to diffuse imagewise into the layer in which the azo compound is present and there to imagewise reduce the azo compound, (e) causing the liberated diffusible dye to diffuse imagewise to the receiving layer, and (f) fixing the dye in the receiving layer thereby to form a dye image.

In another special method of the process as just defined there is provided a process for the production of a photographic image which comprises (a) imagewise exposing a photographic assembly which comprises, at least during the processing steps, a silver halide emulsion layer and present in the silver halide emulsion layer or in a separate layer in operative contact therewith an azo compound as just defined and a dye receiving layer, (b) treating the exposed photographic assembly with a solution or dispersion of a redev compound (as hereinbefore defined) thereby to develop the latent silver image in the silver halide emulsion layer but in the non-latent image areas reducing the azo compound and liberating the diffusible dye if the azo compound is present in the silver halide emulsion layer or if it is not present in the silver halide emulsion layer to diffuse imagewise to the layer which comprises the azo compound and there to reduce the azo compound and to liberate the diffusible dye, (c) causing the liberated diffusible dye to diffuse imagewise to the receiving layer, and (d) fixing the diffused dye in the receiving layer thereby to form a dye image.

Particularly suitable compounds of formula (2) for use in the process of the present invention are compounds of the formula

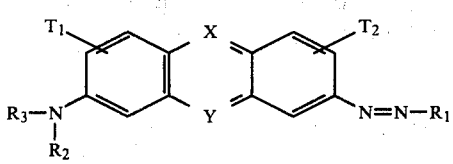  (4)

where X is N or CR$_4$ where R$_4$ is a hydrogen atom or an optionally substituted alkyl or aryl group, Y is S$^\oplus$, N$^\oplus$R$_5$, O$^\oplus$ or N where R$_5$ is an optionally substituted alkyl or aryl group, R$_1$ is a substituted aromatic or heterocyclic group containing a ballasting group, R$_2$ and R$_3$ are each hydrogen atoms or alkyl groups having 1 to 4 carbon atoms, or R$_2$ and R$_3$ together with the nitrogen atom complete a heterocyclic ring, or one of R$_2$ or R$_3$ can be hydrogen and the other of R$_2$ or R$_3$ can be aryl, and T$_1$ and T$_2$ represent hydrogen atoms, substituents or form an annelated benzene ring.

Examples of such further substituents are alkyl of 1 to 4 carbon atoms and particularly methyl, amino and halogen atoms (fluorine, chlorine, bromine).

R$_4$ is preferably hydrogen, alkyl of 1 to 4 carbon atoms, phenyl or phenyl substituted by alkyl of 1 to 4 carbon atoms, halogen, hydroxy or carboxyl.

Preferably R$_5$ has the meaning of R$_4$ except hydrogen.

R$_2$ and R$_3$ are each hydrogen or alkyl of 1 to 4 carbon atoms, or R$_2$ and R$_3$ together with the nitrogen atom complete a 5- or 6-membered heterocyclic ring, or one of R$_2$ or R$_3$ can be hydrogen and the other one can be phenyl, and T$_1$ and T$_2$ represent hydrogen alkyl of 1 to 4 carbon atoms, especially methyl, or each constitutes an annelated benzene ring.

Preferably the group R$_1$ comprises an aromatic or heterocyclic ring containing a hydroxy or dialkylamino group with 1 to 18 carbon atoms in the alkyl moieties ortho or para to the azo link as well as a ballasting group.

A particularly useful group R$_1$ is the group of the formula

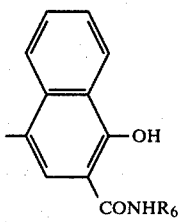  (5)

where R$_6$ is either an alkyl group containing at least 10 carbon atoms or a group containing such an alkyl group or an aryl-ballasting group.

An example of an aryl ballasting group is the group

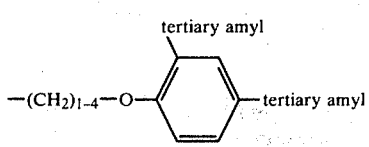

Another useful group R$_1$ is the group of the formula

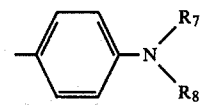  (6)

where R$_7$ and R$_8$ are both alkyl groups having together at least 12 carbon atoms. Compounds of formula (4) may be prepared by diazotising a compound of formula

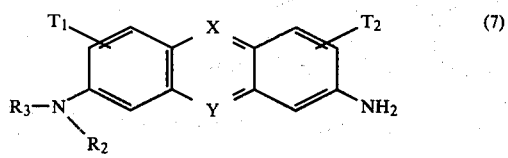  (7)

to yield the diazo compound of formula

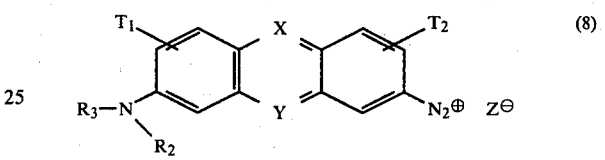  (8)

and then coupling the diazo compound of formula (8) with a coupler of the formula R$_1$$^\ominus$A$^\oplus$ in alkaline conditions where X, Y, R$_1$, R$_2$ and R$_3$ have the meanings assigned to them above, Z$^\ominus$ is an anion and A$^\oplus$ is a cation.

The general formula (7) covers several well-known classes of dyes for example, compounds of formula (4) wherein X is N and Y is N$^\oplus$-R$_5$ are azo-phenazine compounds.

Particularly suitable azo-phenazine compounds of formula (4) are azo-phenazines of formula

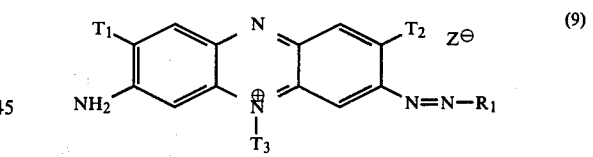  (9)

where R$_1$ has the meaning assigned to it above, T$_1$ and T$_2$ are hydrogen or substituents, in particular methyl, T$_3$ is a phenyl or alkyl group e.g. of 1 to 4 carbon atoms, and Z$^\ominus$ is an anion. Preferably Z$^\ominus$ is tetrafluoroborate. However sometimes the compound exists in the zwitterionic form, especially when R$_1$ is a group of formula (5). Preferably T$_3$ is a phenyl group. When the azo link is cleaved a diffusible magenta phenazine dye is released.

An example of such an azo-phenazine compound is the compound of formula

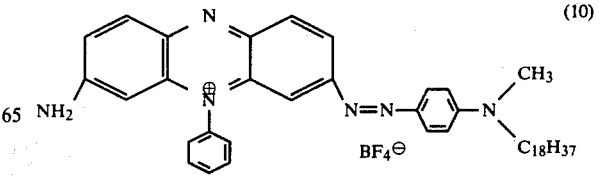  (10)

Another example of such an azo-phenazine compound is the compound of formula

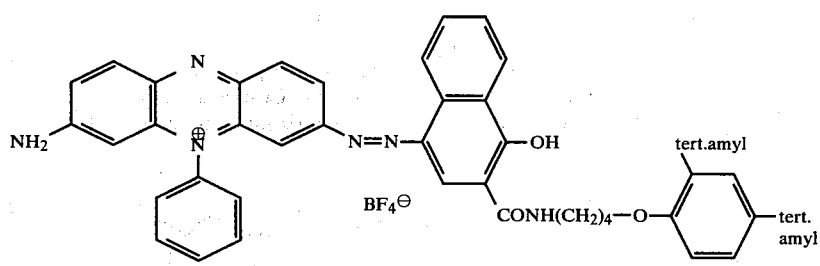

(11)

Compounds of formula (6) wherein X is N and Y is O⊕ are azo-oxazine compounds.

Particularly suitable azo-oxazine compounds of formula (4) are azo-oxazine compounds of formula

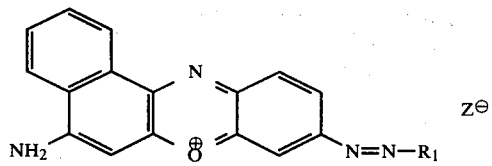

(12)

where Z and $R_1$ have the meanings assigned to them above.

When the azo linkage is cleaved a diffusible blue or bluish oxazine dye is released.

An example of such an azo-oxazine compound is the compound of formula

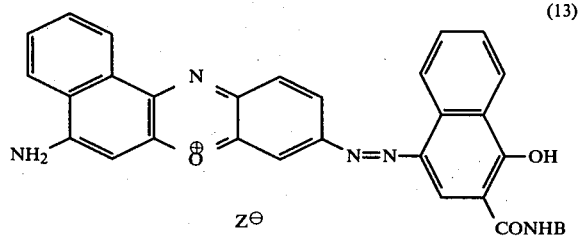

(13)

where B is the group

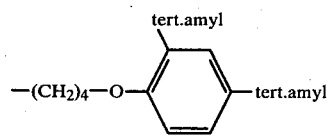

and Z⊖ has the meaning assigned to it above.

Compounds of formula (4) wherein X is N and Y is S⊕ are azo-thiazine compounds.

Particularly suitable azo-thiazine compounds of formula (4) are azo-thiazine compounds of formula

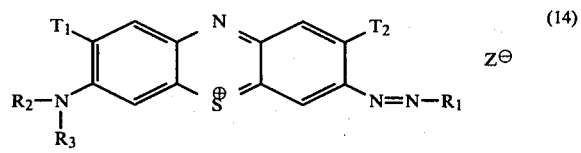

(14)

where $T_1$, $T_2$, Z⊖, $R_1$, $R_2$ and $R_3$ have the meanings assigned to them above.

When the azo-linkage is cleaved a blue to magenta diffusible thiazine dye is released.

An example of such an azo-thiazine compound is the compound of formula

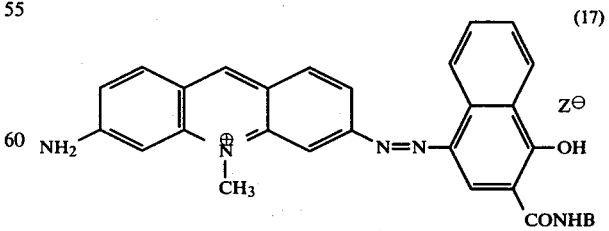

(15)

where B and Z⊖ have the meanings assigned to them above.

Compounds of formula (4) wherein X is $CR_4$ and Y is N⊕ $R_5$ are azo-acridine compounds of formula (16)

where Z, $R_1$, $R_4$ and $R_5$ have the meanings assigned to them above.

When the azo linkage is cleaved a yellow diffusible acridine dye is released.

An example of such an azo-acridine compound is the compound of formula (17)

where B and Z have the meanings assigned to them above.

Other suitable azo-acridine compounds of formula (4) are azo-acridine compounds of formula

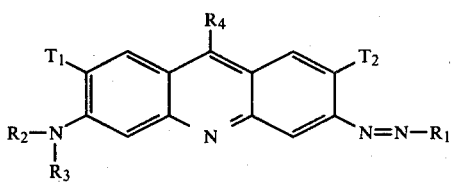
(18)

where $R_1$, $T_1$, $T_2$, $R_2$, $R_3$ and $R_4$ have the meanings assigned to them above.

When the azo linkage is cleaved a yellow diffusible acridine dye is released.

An example of such an azo-acridine compound is the compound of formula

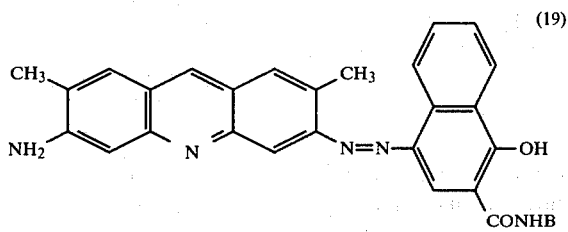
(19)

where B has the meaning assigned to it above.

Compounds of formula (4) wherein X is $CR_4$ and Y is $O^\oplus$ are azo-pyrylium compounds.

Particularly suitable azo-pyrylium compounds of formula (4) are azo-pyrylium compounds of formula

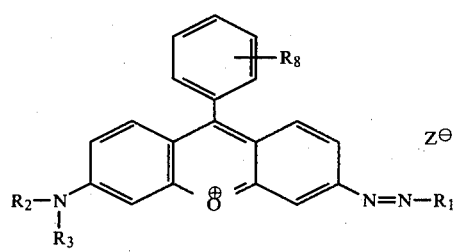
(20)

where $R_1$, $R_2$, $R_3$ and $Z^\ominus$ have the meanings assigned to them above and $R_8$ is a substituent or hydrogen. Examples of these substituents are —COOH, alkyl, e.g. of 1 to 4 carbon atoms and halogen, e.g. chlorine or bromine. Preferably $R_8$ is —COOH $R_2$ and $R_3$ are each hydrogen.

When the azo linkage is cleaved a yellow-magenta diffusible pyrylium dye is released.

An example of such an azo-pyrylium compound is the compound of formula

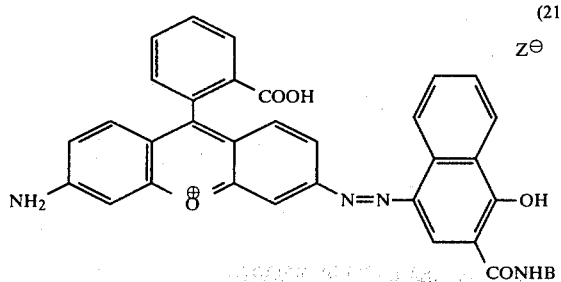
(21)

where B and Z have the meanings assigned to them above.

Other compounds of formula (2) for use in the process of the present invention are azo- or hydrazoanthraquinone compounds of the general formula

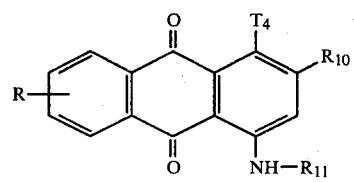
(22)

where R is hydrogen or a substituent, $T_4$ is a hydrogen atom, an hydroxy or alkoxy group, or an amino or substituted amino group, $R_{10}$ is hydrogen or halogen, alkoxy, amino or substituted amino, an aryl or substituted aryl group or a group conferring solubility in water and $R_{11}$ is a group which comprises an azo linkage and a ballasting group or completes the hydrazo linkage and comprises a ballasting group.

Preferred are those compounds of formula (22), wherein $T_4$ is hydrogen, hydroxy, alkoxy of 1 to 4 carbon atoms, especially methoxy or ethoxy, amino (—$NH_2$), mono- or dialkyl($C_1$-$C_4$)amino, or acylamino such as acetylamino, $R_{10}$ is hydrogen, halogen(chlorine, bromine), alkoxy of 1 to 4 carbon atoms, amino, mono- or dialkyl($C_1$-$C_4$)amino, acylamino, such as acetylamino, phenyl or phenyl substituted by halogen alkyl($C_1$-$C_4$) or —$SO_3H$.

Preferred groups conferring solubility in water are sulfonate or carboxylate groups.

The substituents R to the benz ring to which the group —NH—$R_{11}$ is not attached include hydroxy, halogen, amino, alkoxy and sulphonate as mentioned before. The preferred ballasting groups are those as mentioned hereinbefore.

When the azo linkage is cleaved in compounds of formula (22) where $T_4$ is a hydrogen atom a diffusible yellow or orange anthraquinone dye is liberated.

When the azo linkage is cleaved in compounds of formula (22) where $T_4$ is an amino or alkyl amino group a diffusible blue anthraquinone dye is liberated.

When the azo linkage is cleaved in compounds of formula (22) where $T_4$ is an acyl amino group a diffusible red anthraquinone dye is liberated.

When the azo linkage is cleaved in compounds of formula (22) when $T_4$ is an hydroxy or alkoxy group a diffusible magenta anthraquinone dye is liberated.

Suitable azo-anthraquinone compounds of formula (22) are azo-anthraquinone compounds of formula

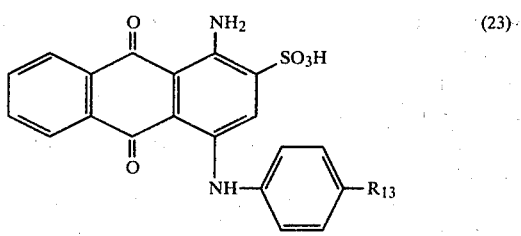
(23)

where $R_{13}$ is a group containing an azo group and a ballasting group.

Compounds of formula (23) may be prepared by diazotising a compound of formula

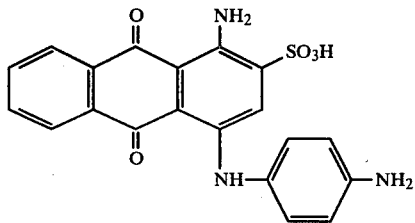

to yield a diazo compound of the formula

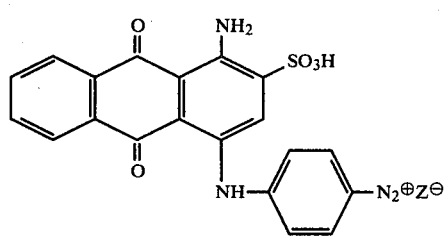

where $Z^{\ominus}$ is an anion and then coupling the diazo compound of formula (25) with a coupler of the formula $R^{\ominus}A^{\oplus}$ where $A^{\oplus}$ is a cation and $R_1^{\ominus}$ has the meaning assigned to it above, in alkaline conditions.

An example of an azo-anthraquinone compound of formula (23) is the compound of formula

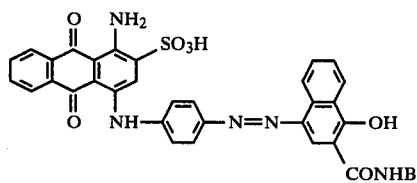

where B is as defined above.

Another class of useful azo-anthraquinones of general formula (23) are compounds of the formula

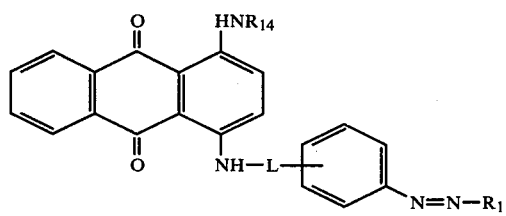

where $R_1$ has the meaning assigned to it above, $R_{14}$ is an alkyl group having 1 to 4 carbon atoms or an optionally substituted aryl (phenyl) group or a hydrogen atom, and L is a linking group.

Examples of suitable linking groups include amide groups, quaternary ammonium groups, or phenyl groups, preferably substituted with groups such as sulphonic acid group to help solubilise the anthraquinone dye which is liberated when the azo linkage is cleaved. A preferred linking group is an alkylene group of 2 to 6 carbon atoms interrupted by a quaternary ammonium group, such as

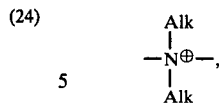

wherein Alk is alkyl of 1 to 4 carbon atoms.

Compounds of formula (25) may be prepared for example either by diazotising a compound of the general formula

 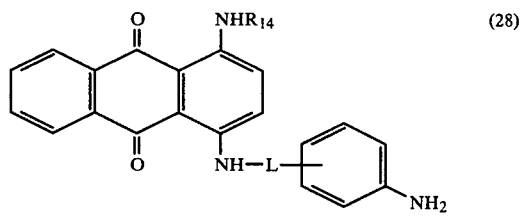

where $R_{14}$ and L have the meanings assigned to them above and then coupling the resultant diazo compound with a coupler of the formula $R_1^{\ominus}A^{\oplus}$ where A is a cation and $R_1^{\ominus}$ has the meaning assigned to it above or by reacting a compound of the formula

 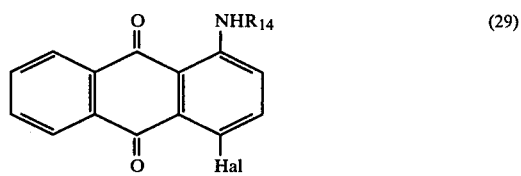

where $R_{14}$ has the meaning assigned to it above with a preformed azo compound of the formula

 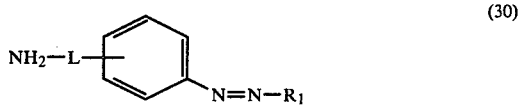

where Hal is a halogen atom and $R_1$ and L have the meanings assigned to them above.

An example of an azo-anthraquinone compound of formula (27) is the compound of formula

 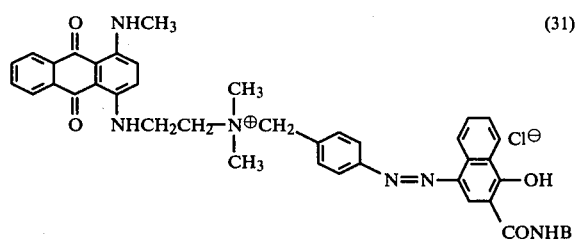

where B has the meaning assigned to it above.

Another example of an azo anthraquinone of formula (27) is the compound of formula

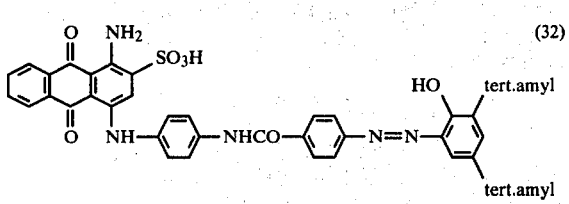
(32)

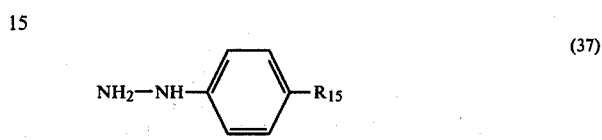
(33)

Alternatively compounds of general formula (27) may be made by forming the —L— group from anthraquinone and azo precursors. For instance, the compound of formula (32) may be made by reacting a compound of formula (24) with an azo compound of formula

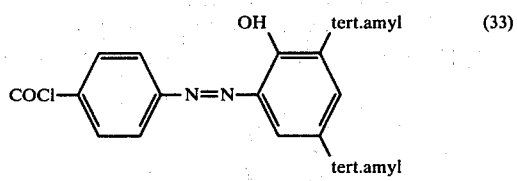
(33)

Another group of useful azo-anthraquinones of formula (22) are azo-anthraquinones of formula

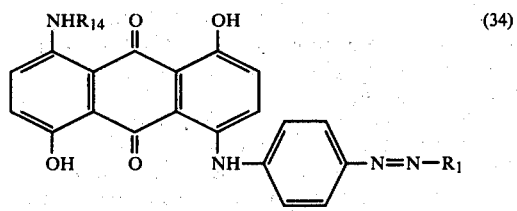
(34)

where $R_1$ and $R_{14}$ have the meanings assigned to them above.

Compounds of formula (34) may be made in a similar manner to compounds of formula (23), that is to say diazotisation of a compound of formula

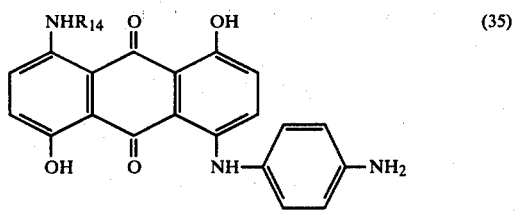
(35)

followed by coupling with a coupler $R_1 \ominus A^\oplus$ where $A^\oplus$ is a cation and $R_1$ and $R_{14}$ have the meanings assigned to them above.

Another useful group of compounds of general formula (22) are hydrazo-anthraquinones of formula

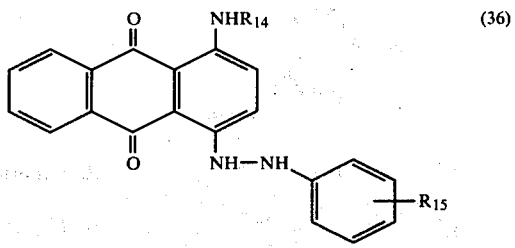
(36)

where $R_{14}$ has the meaning assigned to it above and $R_{15}$ is either an alkyl group containing at least 10 carbon atoms or is a group which comprises such an alkyl group (alkoxy or alkylmercapto of 10 to 24, preferably of 10 to 18 carbon atoms), or is a ballasting aryl group as mentioned hereinbefore.

Hydrazo-anthraquinones of formula (36) may be prepared by reacting a compound of the formula (29) with a substituted phenyl hydrazine of the formula

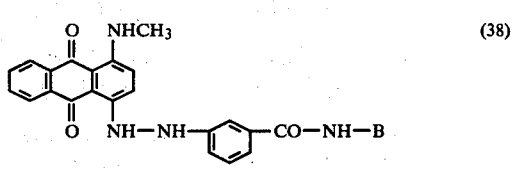
(37)

where $R_{15}$ has the meaning assigned to it above, in an alkaline medium.

An example of hydrazo-anthraquinone of formula (36) is the compound of formula

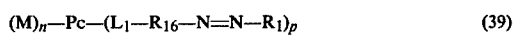
(38)

where B has the meaning assigned to it above.

Another group of azo compounds of formula (1) of use in the process of the present invention consists of the azophthalocyanine compounds of formula $$(M)_n-Pc-(L_1-R_{16}-N=N-R_1)_p \qquad (39)$$

where M is a metal n is 0 or 1, Pc represents a phthalocyanine complex, $L_1$ is a linking group, $R_1$ has the meaning assigned to it above, p is 1 to 4 and $R_{16}$ is an optionally substituted aromatic or heterocyclic ring.

Examples of M are copper, cobalt, iron, nickel, magnesium, manganese, barium and zinc.

Preferably M is copper and n is 1 and p is 2.

Preferably $L_1$ is either a short linking group or comprises a solubilising moiety for example a quaternary ammonium group.

Preferably $R_{16}$ is a phenyl group optionally substituted by alkyl or alkoxy of 1 to 4 carbon atoms, halogen or hydroxy.

When the azo linkage is cleaved a diffusible cyan dye is released.

A phthalocyanine complex can be shown as formula

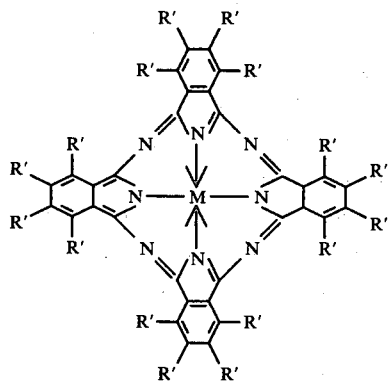
(40)

where M is the metal which may or may not be present (but when it is not present it is replaced with two H atoms) and each R' can be hydrogen, chlorine or bromine, $SO_3H$ or $SO_3W$, where W is Na, K or $NH_4$.

In the phthalocyanines of formula (40) at least 1 but no more than 4 of R' of formula (40) are a group of the formula $$-L_1-R_{16}-N{=}N-R_1 \quad (41)$$

where $L_1$, $R_1$ and $R_{16}$ have the meanings assigned to them above.

Preferably all the groups of formula (41) attached to the phthalocyanine complex are the same but they can be different.

Phthalocyanine complexes are described in General Synthetic Procedures for Phthalocyanine Dyes in Chapter 5 of E. H. Moser and A. L. Thomas, Phthalocyanine Compounds, Reinhold, published 1963.

A preferred group $L_1$ is of the formula

(42)

A particularly useful phthalocyanine of formula (40) is the compound of formula

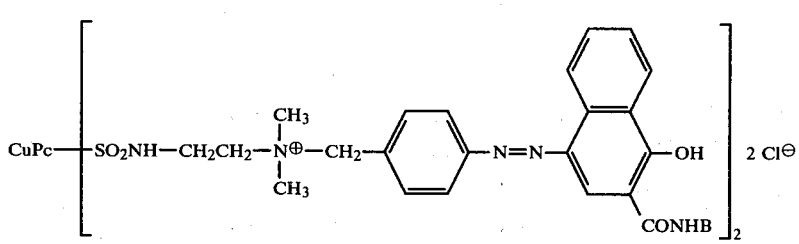
(43)

where B has the meaning assigned to it above.

Usually the first step in the preparation of the azophthalocyanine compounds of formula (41) is to prepare a compound of formula

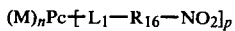
(44)

where $L_1$, M, n, Pc, $R_{16}$ and p have the meanings assigned to them above.

The second step is to reduce the $NO_2$ to $NH_2$ and then diazotise the $NH_2$. Then couple 1 mole of the diazo compound of the formula

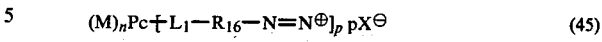
(45)

where $L_1$, M, n, Pc, $R_{16}$, H and p have the meanings assigned to them above and $X^\ominus$ is an anion, with p moles of a coupler of the formula $R_1\ominus A\oplus$ where $R_1$ has the meaning assigned to it above and $A\oplus$ is a cation.

In the case of the compounds of formula (2) and (3) when D also contains an azo link the only suitable ones are those in which the azo group in the residue D is more stable to reduction than the —N=N— linkage of azo compounds of formula (2) or the —NH—NH— linkage of the hydrazo compounds of formula (3).

An example of a suitable class of azo compounds of formulae (2) are compounds of the general formula

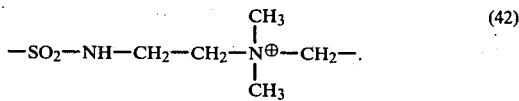
(46)

where $R_1$ has the meaning assigned to it above, L is either a linking group or a direct link, V is a group which comprises an aromatic or heterocyclic ring, at least one of the groups L and V comprises an active methylene group.

It is thought that the group $R_1$ renders the azo link to which it is attached more readily cleavable by the reducing compound than the other azo link in the compound. This other azo link is stabilised against reduction by the presence of the group which comprises the active methylene group attached thereto.

Examples of groups which comprise an active methylene group are pyrazolones, hydroxypyridones and the ketomethylene group —CO—$CH_2$—CO—.

A group of suitable azo compounds of formula (46) have the active methylene group in group V. These compounds are of the general formula

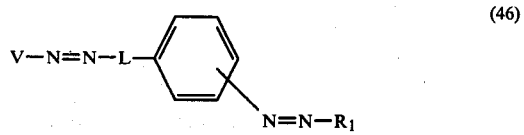
(47)

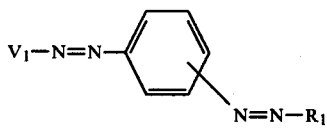

where $V_1$ is a group which comprises an active methylene group.

Compounds of formula (47) may be prepared by coupling a diazo compound of the formula

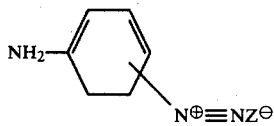 (48)

where Z is an anion, with a coupler of the formula $R_1^\ominus A^\oplus$ to yield a compound of the formula

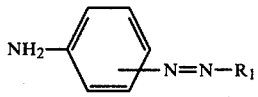 (49)

where in the above formulae $R_1$ has the meaning assigned to it above and $A^\oplus$ is a cation, diazotising the compound of formula (49) to yield the compound of formula

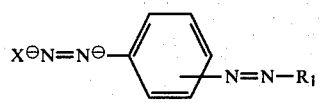 (50)

where $R_1$ has the meaning assigned to it above and coupling the compound of formula (50) with a coupler of the formula $V_1^\ominus A^\oplus$ where $V_1$ has the meaning assigned to it above and A is a cation to yield a compound of formula (47).

An example of a compound of formula (47) is the pyrazolone group-containing compound of formula

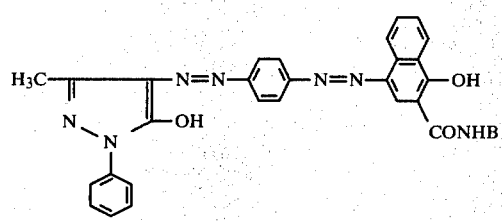 (51)

where B has the meaning assigned to it above.

Another example of a compound of formula (47) is the hydroxypyridone group-containing compound of formula

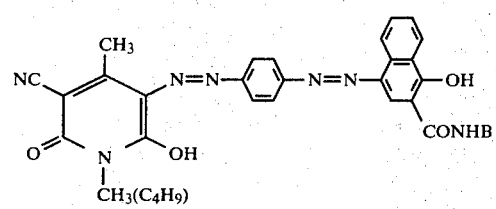 (52)

where B has the meaning assigned to it above.

Another group of suitable azo compounds of formula (46) have the group containing the active methylene group in the linking group L. These compounds are of the general formula

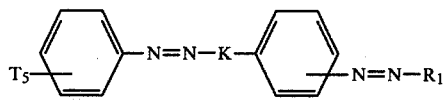 (53)

where $T_5$ is at least one substituent, K is a group which contains an active methylene group and $R_1$ has the meaning assigned to it above. Examples of substituents $T_5$ are alkyl or alkoxy each of 1 to 4, preferably of 1 to 2, carbon atoms, a substituted amino group, for example a mono- or dialkylamino group wherein alkyl contains 1 to 4, preferably 1 to 2 carbon atoms, a halogen atom (chlorine, bromine), carboxyl or an amide group.

The azo compounds of formula (53) are of special interest as the substituents $T_5$ determine to a great extent the colour of the dye released when the azo link to which $R_1$ is attached is broken. For example, when $T_5$ is 4-methoxy the liberated dye is yellow. When it is 3,4-dimethoxy a darker yellow dye is liberated. When it is 4-diethylamino the dye is reddish-orange.

Compounds of formula (53) may be prepared by diazotising a compound of formula

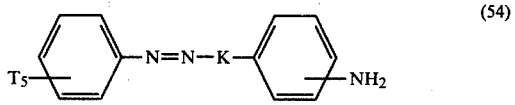 (54)

to yield a diazo compound of formula

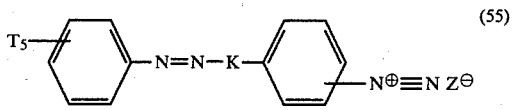 (55)

and then coupling this compound with a coupler of the formula $R_1^\ominus A^\oplus$ to yield a compound of formula (53), where in the above formula $T_5$ and K have the meanings assigned to them above, $A^\oplus$ is a cation and $Z^\ominus$ is an anion.

A particular class of compounds of formula (53) are the compounds where K is a pyrazolone radical. These compounds have the general formula

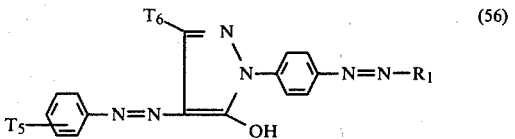 (56)

where $T_5$ and $R_1$ have the meanings assigned to them above and $T_6$ is hydrogen or a substituent, for example alkyl of 1 to 4 carbon atoms, especially methyl.

An example of a compound of formula (56) is the compound of formula

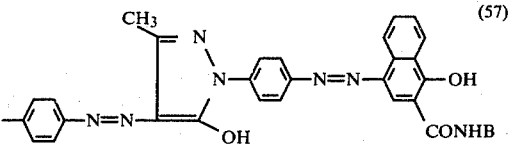 (57)

where B has the meaning assigned to it above.

Compounds of formula (53) often occur in the hydrazo form which is written as formula

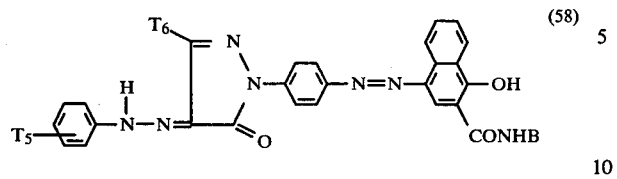 (58)

where all the symbols have the meanings assigned to them above.

A suitable azoxy compound for use in the process of the present invention is the compound of formula

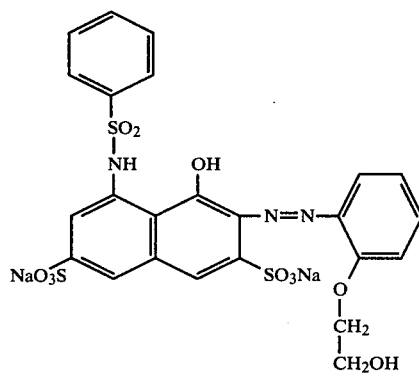 (59)

This is a known compound.

The azo compounds may be incorporated in the layer of the photographic material using any of the methods employed for incorporating colour couplers into normal photographic material or azo dyes into silver dye bleach material. Such methods include aqueous solution or dispersion and oil dispersion.

Another class of useful compounds of formula (1) are compounds of the general formula

 (60)

or of the general formula

 (61)

where in the above two formulae D and BAL have the meanings assigned to them above and $R_{17}$, $R_{18}$ and $R_{19}$ each represent a hydrogen atom or an alkyl group with 1 to 3 carbon atoms, and the reduction potential of $-N=CR_{17}-$ or the $-NR_{18}-CR_{17}R_{19}-$ bond is above $-200$ mV measured against a standard hydrogen electrode at a pH of less than 3.

It is to be understood that the photographic assembly may comprise more than one silver halide photosensitive system having associated therewith either an imino compound of formula (60) or an amino compound of formula (61) or may comprise one or more silver halide photosensitive systems having associated therewith either an azo compound of formula (2) or a hydrazo compound of formula (3).

The amino compounds of formula (61) are derivatives of the imino compounds of formula (60), thus for ease of reference the term "imino compounds" as used hereinafter also covers the derived amino compounds and refers to compounds of formulae (60) and (61).

Particularly useful compounds of formula (60) and of formula (61) are compounds of the general formula

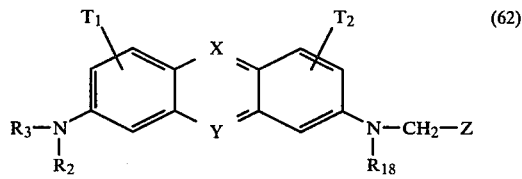 (62)

or of the general formula (63)

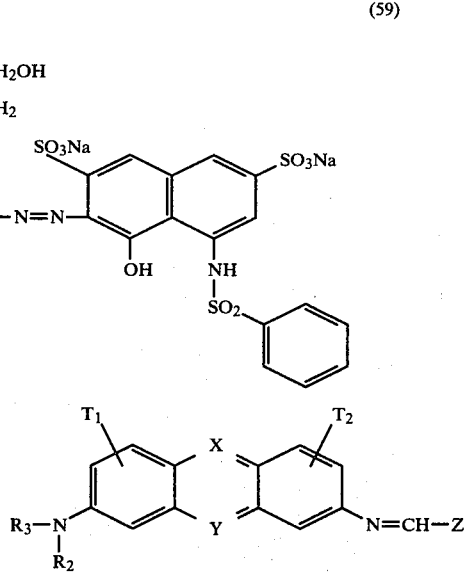

wherein $T_1$, $T_2$, $R_2$, $R_3$, $R_{18}$, X and Y have the meanings assigned to them above, and Z is a group which comprises both an activating group (as hereinafter described) which contains at least one double bond system and also a ballasting group.

The compounds of formula (63) are the partially oxidised compounds of formula (62).

By activating group is meant a group, preferably an electron withdrawing groups, which activates the $-NR_{18}-CH_2-$ or $-N=CH-$ bond and renders it more susceptible to reductive cleavage. Examples of suitable activating groups which contain a double bond system are aromatic rings and groups which contain a carbonyl group.

A particularly useful group Z is the group of the general formula

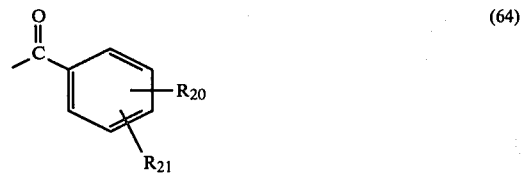 (64)

where $R_{20}$ comprises a ballasting group containing at least 10 carbon atoms and $R_{21}$ represents a substituent such as alkyl, substituted alkyl or halogen or is preferably hydrogen.

The ballasting group may be for example alkyl or alkoxy of 10 to 24 carbon atoms, preferably alkoxy of 14 to 18 carbon atoms.

Another useful group Z is of the general formula

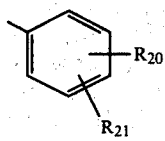
(65)

where $R_{20}$ and $R_{21}$ have the meanings assigned to them above.

A further useful group Z is of the general formula

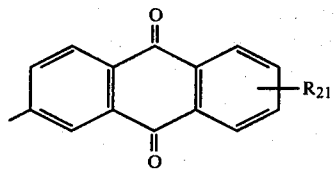
(66)

where $R_{21}$ has the meaning assigned to it above.

For example when X is N and Y is $O^\oplus$ the compounds of formulae (62) and (63) are oxazine compounds. Particularly useful dyes are of formula

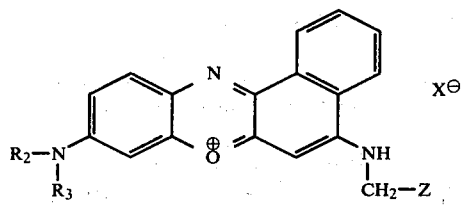
(67)

where $X^\ominus$ is an anion and $R_2$ and $R_3$ are as defined above. An example of such an oxazine compound is the compound of formula

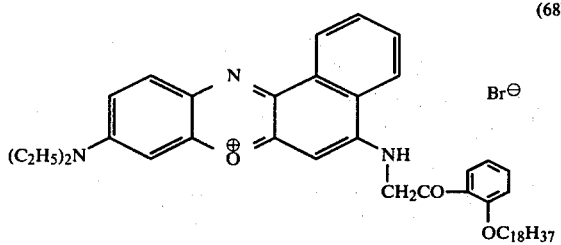
(68)

An oxazine compound of formula (63) is the compound of formula

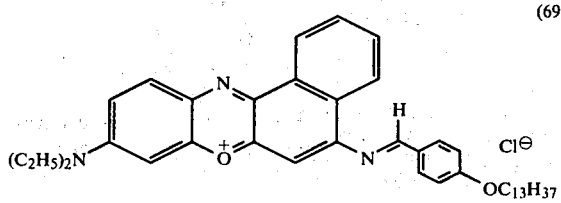
(69)

Compounds of formula (62) wherein X is N and Y is $NR_5^\oplus$ are phenazine dyes. Particularly useful phenazine compounds of formula (62) are the dyes of formula

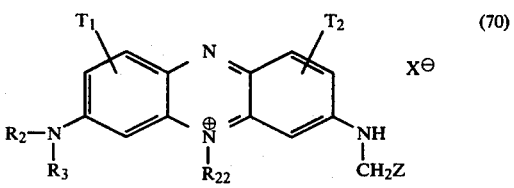
(70)

where $R_2$, $R_3$, $T_1$, $T_2$, X and Z have the meanings assigned to them above and $R_{22}$ is a hydrogen atom, alkyl (of 1 to 4 carbon atoms) and is preferably a phenyl group. An example of such a phenazine compound is the compound of formula

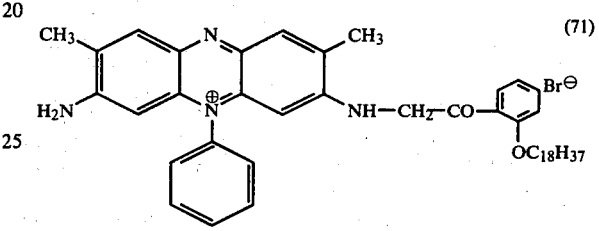
(71)

Compounds of formula (62) where X is N and Y is $S^\oplus$ are thiazine dyes. Useful thiazine compounds have the formula

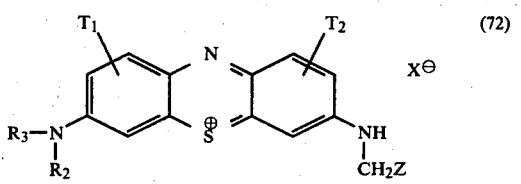
(72)

where $T_1$, $T_2$, $R_2$, $R_3$, $X^\ominus$ and Z have the meanings assigned to them above and $T_2$ preferably comprises a methyl group. An example of such a thiazine compound is the compound of formula

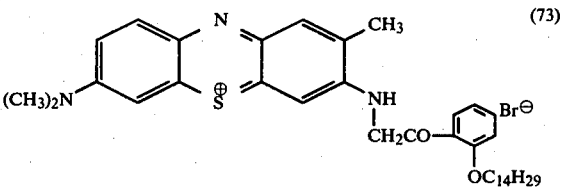
(73)

Compounds of formula (62) may be prepared by treating a dye of formula

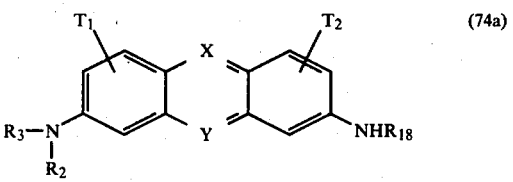
(74a)

with alkali and a suitable alkylating agent of formula

  (75)

where G is a leaving group, and X, Y, Z, $R_2$, $R_3$, $R_{18}$, $T_1$ and $T_2$ have the meanings assigned to them above. An example of a leaving group is halogen, especially Br.

Compounds of formula (63) may be made by condensating a dye of formula

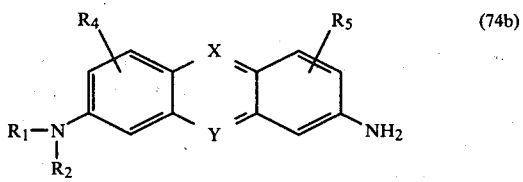  (74b)

where X, Y, $R_1$, $R_2$, $R_4$ and $R_5$ have the meanings assigned to them above with a substituted aldehyde of formula Z-CHO where Z has the meaning assigned to it above.

In the azo compounds of formula (2) of use in the process of the present invention D is linked to the azo group by a covalent bond. Also in the imino and amino compounds of formulae (60 and (61) D is linked to the imino and amino groups by a covalent bond. However in another class of azo dyes of particular use in the process of the present invention the group which contains the preformed dye consists of a preformed dye $D^1$ linked to the remainder of the group D by an ionic bond.

Compounds of this type are of the general formula

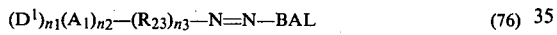  (76)

where $A_1$ is a charged group which may be positively or negatively charged, $D^1$ is a residue of a diffusible dye which carries a charge opposite in sign to the charge carried by $A_1$, $R_{23}$ is an optionally substituted aromatic or heterocyclic ring which is present unless $A_1$ is a charged heterocyclic group, $n_1$ is 1 or 2, $n_2$ is 1 or 2, $n_3$ is 0 or 1 and BAL has the meaning assigned to it above. Examples of substitution in $R_{23}$ which is for example phenyl, naphthyl or pyridyl include alkyl or alkoxy groups ($C_1$-$C_4$) and halogen atoms (fluorine, chlorine, bromine) or hydroxy.

Thus in the formula (76) the group $(D^1)_{n1}(A_1)_{n2}$—$(R_{23})_{n3}$ is the group D of formula (1).

Examples of group $A_1$ which are positively charged are a quaternary ammonium group, a quaternary phosphonium or arsonium group and a guanidinium group.

Examples of group $A_1$ which are negatively charged are a sulphonic acid anion group, a phosphonic acid anion group and an alkyl sulphate group.

Examples of suitable classes of dyes for the residue of the diffusible dye $D^1$ are phthalocyanines, anthraquinones and azines, including oxazines and thiazines, and acridines. Also indigo dyes, oxonols, pyrylium dyes, azo and azoxy dyes are useful.

When $A_1$ in formula (76) is anionic the compounds of formula (76) may be prepared from compounds of formula

  (77)

where $A_1$, $R_{23}$, BAL, $n_1$, $n_2$ and $n_3$ have the meanings assigned to them above and M is a cation, by reaction with a cationic or basic dye such as those described in the Colour Index.

Mixed solutions of a suitable cationic or basic dye and a compound of formula (77) result in a precipitation of a compound of formula (76). The precipitated compound can then be purified. Alternatively the mixed solution may be an aqueous gelatin solution and in this case a gelatin suspension of the compound of formula (76) is produced which can then be added to a photographic coating solution to coat onto a film base.

However the compounds of formula (76) may be prepared in situ in a coated gelatin layer. In this case a gelatin coating which comprises a compound of formula (77) is prepared and a solution of a cationic dye applied thereto. A compound of formula (76) is then produced in situ in the coated gelatin layer.

Im similar manner when $A_1$ is cationic compounds of formula (76) may be prepared from compounds of formula

  (78)

where $A_1$, $R_{23}$, BAL, $n_1$, $n_2$ and $n_3$ have the meanings assigned to them above and $X^\ominus$ is an anion, using soluble anionic or acid dyes such as those listed in the Colour Index.

Compounds of formula (78) may be prepared by diazotising a compound of formula

  (79)

where $A_1$, $R_{23}$, $n_1$, $n_2$ and $n_3$ have the meanings assigned to them above to yield a compound of formula

  (80)

and then coupling this diazo compound with a coupler $R_1\ominus M^\oplus$ where $R_1$ is as defined above and $M^\oplus$ is a cation.

A particularly useful compound of formula (77) is the compound of formula

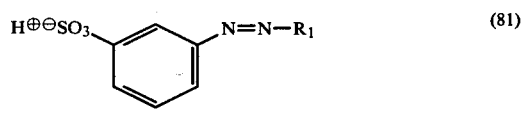  (81)

where $R_1$ is as defined above.

Most preferably $R_1$ has the formula

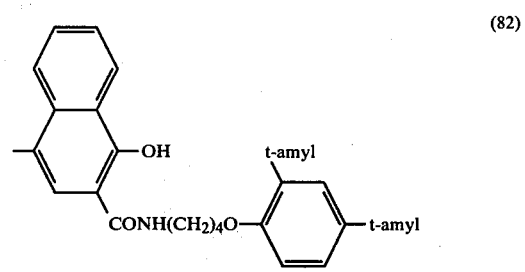  (82)

Suitable basic dyes for the preparation of the compound of formula (78) are basic dyes of the general formula

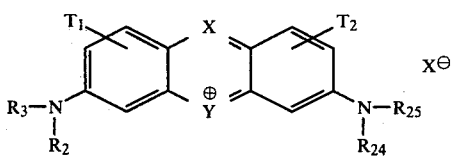
(83)

where $T_1$, $T_2$, $R_2$, $R_3$, X, Y and $X^\ominus$ are as defined above, and $R_{24}$ and $R_{25}$ are hydrogen, alkyl of 1-4 carbon atoms, preferably methyl or ethyl, or optionally substituted aryl (phenyl) groups. The substituents are e.g. alkyl of 1 to 4 carbon atoms, halogen (chlorine, bromine), hydroxy or carboxyl.

Compounds of formula (83) wherein X is N and Y is $NR^\oplus_5$ are phenazine compounds.

Particularly suitable phenazine compounds of formula (83) are phenazines of formula

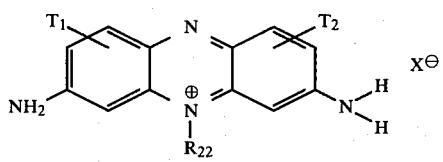
(84)

where $T_1$, $T_2$ and $R_{22}$ are as defined above. Preferably $R_{22}$ is a phenyl group. $X^\ominus$ is an anion.

An example of such a phenazine compound is the compound of formula

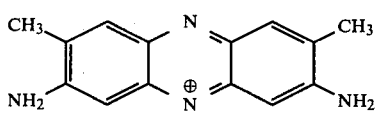
(85)

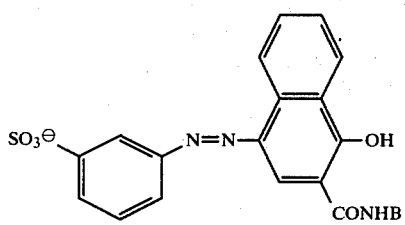

where B is as defined above.

When the azo link is cleaved a magenta dye is liberated.

Compounds of formula (83) wherein X is N and Y is $O^\oplus$ are oxazine compounds.

Particularly suitable oxazine compounds of formula (83) are oxazine compounds of formula

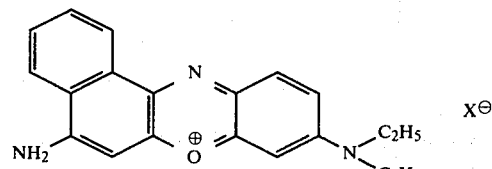
(86)

where $X^\ominus$ is an anion.

An example of such an oxazine compound is the compound of formula

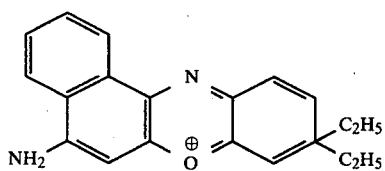
(87)

where B is the group as defined above.

When the azo link is cleaved a diffusible bluish dye is obtained.

Compounds of formula (83) where X is N and Y is $S^\oplus$ are thiazine compounds.

Particularly suitable thiazine compounds are those of formula (88)

where $T_1$, $T_2$, $X^\ominus$, $R_2$, $R_3$, $R_{24}$ and $R_{25}$ have the meanings assigned to them above.

An example of such a thiazine compound is the compound of formula (89)

where B has the meaning assigned to it above.

When the azo link is cleaved a blue dye is liberated.

Compounds of formula (83) where X is $CR_4$ and Y is $N^\oplus R_5$ are acridine compounds.

Particularly suitable acridine compounds are those of formula

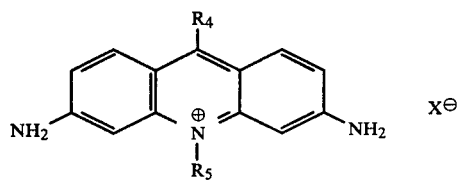
(90)

where $X^{\ominus}$, $R_4$ and $R_5$ have the meanings assigned to them above.

An example of such an acridine compound of formula 90 is the compound of formula

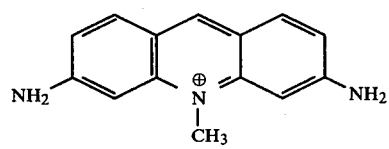
(91)

where B has the meaning assigned to it before.

When the azo linkage is cleaved a diffusible yellow acridine dye is released.

Compounds of formula (83) where X is $CR_4$ and Y is $O^{\oplus}$ are pyrylium compounds.

Particularly suitable pyrylium compounds are compounds of formula

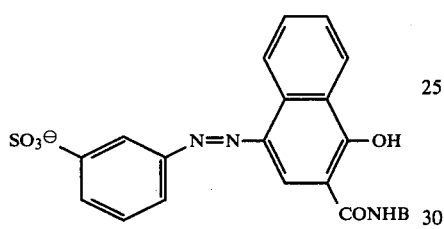
(92)

where $R_2$, $R_3$, $R_{24}$, $R_{25}$ and $X^{\ominus}$ have the meanings assigned to them above and $R_{26}$ is a substituent, such as alkyl of 1 to 4 carbon atoms, halogen (chlorine, bromine, fluorine), hydroxy or carboxyl.

An example of a rhodamine compound of formula (78) is the compound of formula

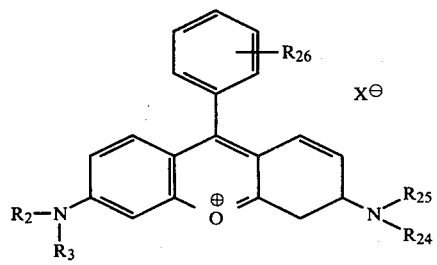
(93)

-continued

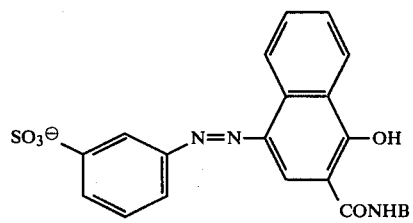

where B is as defined above.

When the azo linkage of dye (93) is cleaved a magenta diffusible rhodamine dye is released.

Another class of basic dyes which are suitable for the preparation of the compounds of the general formula (77) are basic anthraquinone dyes of the general formula

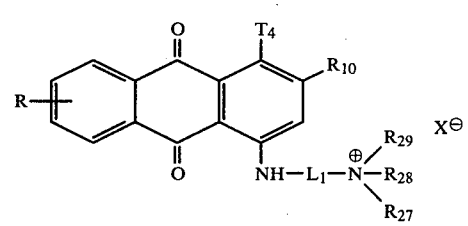
(94)

where $R_1$, $R_{10}$, $T_4$, $X^{\ominus}$ and L are as defined above, $R_{27}$, $R_{28}$ and $R_{29}$ are alkyl or aryl groups. The alkyl groups preferably contain 1 to 4 carbon atoms while aryl is for example phenyl optionally substituted by alkyl or alkoxy of 1 to 4 carbon atoms, halogen (fluorine, chlorine, bromine) or hydroxy.

It is to be understood that further substitution may be present in the anthraquinone nucleus, particularly in the ring which is not already substituted. Alternatively $R_{27}$, $R_{28}$ and $R_{29}$ may comprise a ring system or systems.

An example of such an anthraquinone compound of formula (76) is the compound of formula

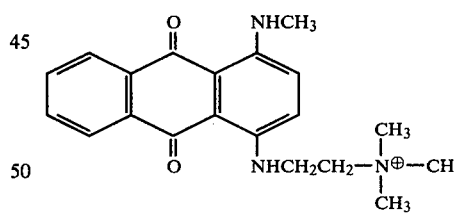
(95)

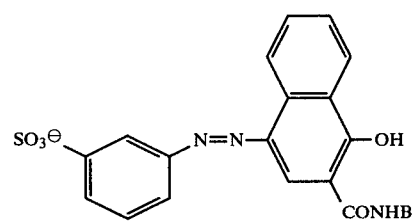

where B has the meaning assigned to it above.

Another class of cationic dyes which is suitable for the preparation of the compounds of formula (76) ionic phthalocyanine dyes.

A phthalocyanine complex can be shown as formula

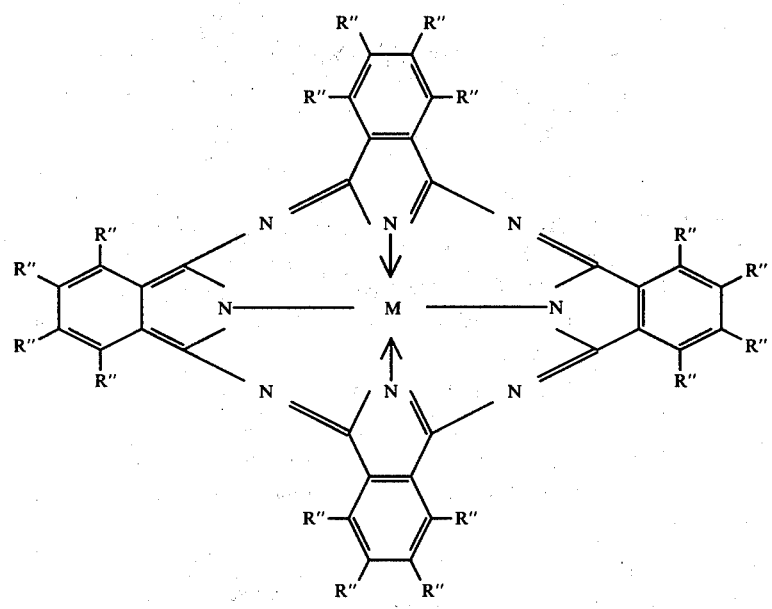
(96)

where M represents a metal which may or may not be present and each R″ can be hydrogen, SO₃H, SO₃W where W is an alkaline metal, especially sodium or potassium, or ammonium, and at least one R″ has the formula L-N⊕R$_{27}$R$_{28}$R$_{29}$ where L, R$_{27}$, R$_{28}$ and R$_{29}$ have the meanings assigned to them above.

M may be iron, nickel or cobalt and is preferably copper. An example of such a phthalocyanine compound of formula (76) is the compound of formula

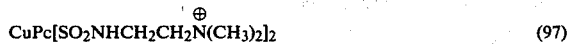
CuPc[SO₂NHCH₂CH₂N(CH₃)₂]₂ (97)

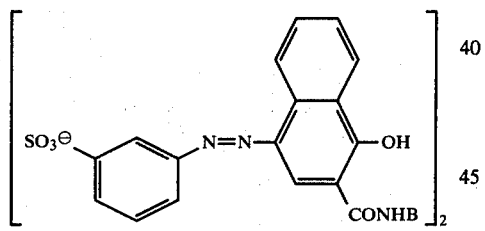

where B has the meaning assigned to it above and Pc represents the phthalocyanine nucleus of formula (96).

Compounds of formula (76) may be prepared by diazotising an amine of formula A—NH₂ where A is either a heterocyclic ring which can be quaternised or represents either an aromatic or heterocyclic ring to which is attached a group which can be converted to a cationic group, and then coupling the resultant diazonium compound of the formula A—N≡N⊕ with a coupler of the formula W⊕BAL⊖ where W and BAL have the meanings assigned to them above and then forming the cationic compound by reaction with a quaternising reagent, e.g. methyl iodide.

An example of such a reaction is when A is

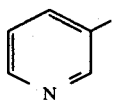

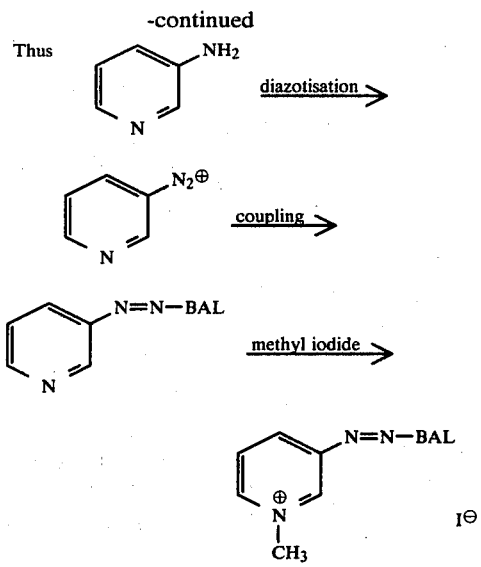

An example of such a compound is the compound of formula

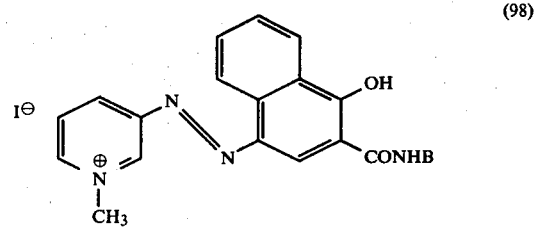
(98)

where B has the meaning assigned to it above.

An example of a group A which can be converted to a cationic group is the group of formula

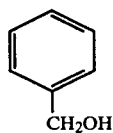

which may be converted to quaternary ammonium groups, phosphonium or arsonium groups by reaction with p-toluenesulphonyl chloride and an amine or phosphine or arsine, thus:

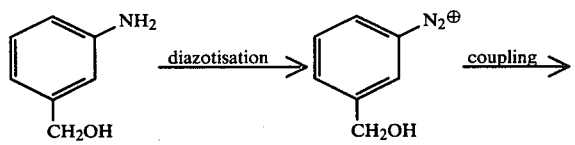

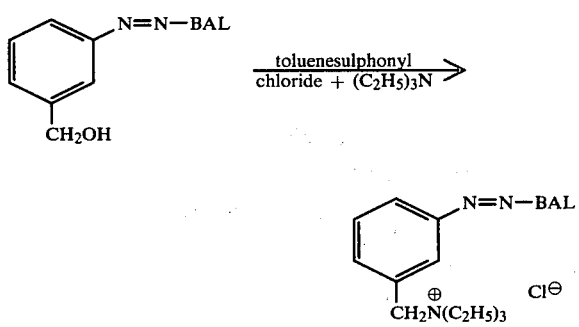

An example of such a compound is the compound of formula

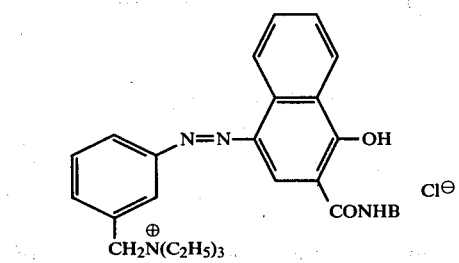

(100)

where B has the meaning assigned to it above.

Diamines of the formula $NH_2$—F—$NH_2$ where F is a linking group are also of use as they can be converted to guanidinium compounds. For example:

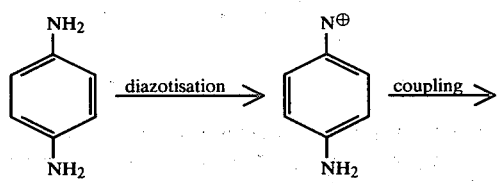

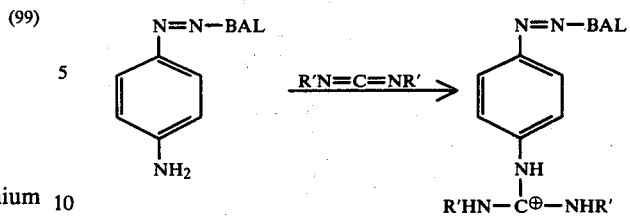

(99)

where R' is hydrogen or alkyl, e.g. of 1 to 6 carbon atoms or cycloalkyl of 5 or 6 carbon atoms, for example cyclohexyl.

Suitable dyes for the formation of compounds of formula (76) where A carries a positive charge include dyes of the azo, anthraquinone and phthalocyanine classes. A suitable azo dye has the structure:

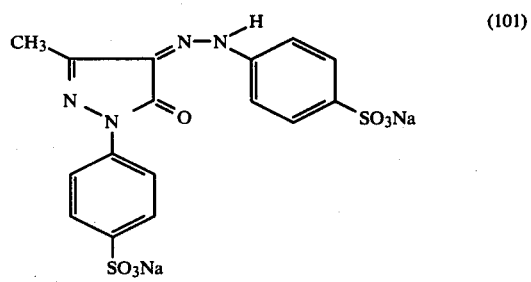

(101)

Thus the compound of formula (76) made using the compounds of formula (100) and formula (101) is of the formula

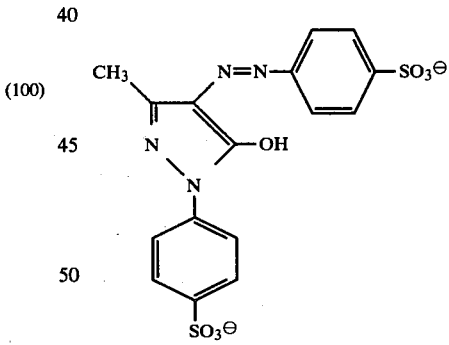

(102)

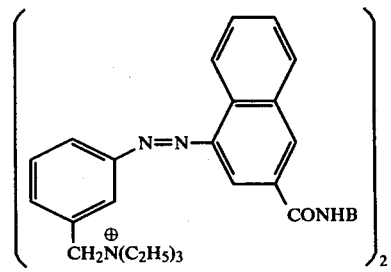

An example of such a phthalocyanine complex is the compound of formula

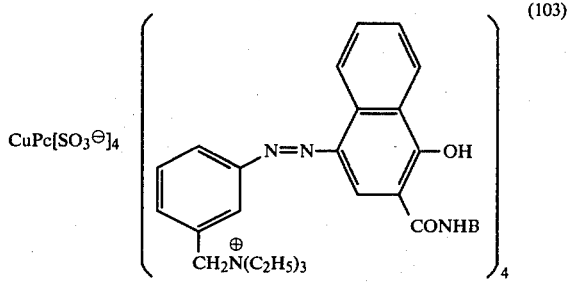

where Pc is the complex of formula (96) and four of R groups are $SO_3^\ominus$.

It is to be understood that sometimes the diffusible dye is in a reduced form, which can be written as $DH_2$, and is preferably oxidised to its full colour density either in its passage to the receiving layer or in the receiving layer. This oxidation may occur in the presence of air or be caused by an oxidant present in the receiving layer or in an extra processing step, for example raising the pH of the assembly.

The photographic assembly contains one or two sections. If the photographic assembly is prepared as two sections, one section comprises the supercoat, the silver halide emulsion layer(s) and the compound of formula (1) and the other section comprises the layer which contains the dye mordant and the support base.

If the photographic assembly is prepared as a single assembly it comprises the supercoat, the silver halide emulsion layer(s), the compound of formula (1) and the dye mordant layer all coated on the support base; optionally there is either a stripping layer or a stripping position between the silver halide emulsion layer(s) and the dye mordant layer.

It is to be understood that the image part of the photographic assembly in both methods A and B, that is to say the portion of the assembly which includes both the receiving layer and a photobase, may be joined initially to the photosensitive portion of the assembly that is to say the portion of the assembly which includes the silver halide emulsion layer and the azo compound; or the photosensitive portion of the assembly and the image portion of the assembly may be separate components which are brought together only during processing. If the photographic assembly comprises a separate image portion not connected initially to the photosensitive portion, after the dye image has been formed in this portion the two components may be separated. However, it is sometimes preferred that after processing the two sheets are retained together. This avoids the production of a disposable photosensitive portion of the assembly.

Preferably when the photographic assembly is in two portions a supercoat layer or some other layer is so formed as to be able to act as a base for the silver halide emulsion layer and the other layers of the photosensitive portion of the assembly.

It is to be understood that the photographic assembly can and usually does include a number of layers other than the silver halide emulsion layer, which preferably also comprises the compound of formula (1) for example an interlayer or layers between the silver halide emulsion layer and the receiving layer. Also there may be a supercoat layer which protects the photosensitive emulsion layer, there may be opaque layers, there may be light reflecting layers, there may be timing layers or there may be a neutralising layer further stripping layers or positions. The photographic assemblies can contain at least one light opaque layer adjacent to a silver halide emulsion layer, for example the light opaque layer can be present on each side thereof. The white reflecting layer can be adjacent to the dye mordant layer on the side remote from the support base. The photographic assembly can also comprise in order a supercoat layer, a light opaque layer, a silver halide emulsion layer, a light opaque layer, a dye mordant layer and a support base, optionally having between the second mentioned light opaque layer and the dye mordant layer a stripping position or stripping layer. Further there may be present between the second metioned light opaque layer and the dye mordant layer a white reflecting layer and also between the second mentioned light opaque layer and the white reflecting layer a stripping position.

Examples of assemblies of use in the present invention are shown in FIGS. 1 to 11 which follow. However these assemblies are merely representative of the very great number of assemblies which can be used in the process of the present invention.

The photographic assembly may as previously described consist of two components, one the image portion and the other the photosensitive portion. After exposure of the silver halide emulsion layer processing liquid is introduced between them or coated on one of the portions and the two portions are brought together in close contact.

When an assembly of this type is used to perform the method B of the present invention the processing fluid may contain a pre-formed redev compound or an inactive form of the redev compound which is able to act neither as silver halide developing agent nor as an —E—F— bond reducing agent. In the second case there may be present in the photosensitive portion of the assembly preferably between the supercoat layer and the silver halide emulsion layer a metallic layer as hereinafter described. When the processing fluid is introduced between the image portion and the photosensitive portion the inactive redev compound diffuses into this metallic layer and there is reduced to its active state. It then diffuses into the silver halide emulsion layer and there the latent image areas of the silver halide are developed by the compound but in the nonlatent image areas the redev compound reduces the compound of formula (1) if this compound is present in the same layer as the silver halide or diffuses imagewise into the layer which comprises the compound of formula (1) and there reduces in an imagewise manner the compound of formula (1). The liberated diffusible dye then diffuses, in both cases, to the receiving layer, i.e. the image portion of the assembly, and the receiving layer may then removed from contact with the photosensitive portion of the assembly. If a preformed redev compound is used in a two-component assembly preferably the supercoat layer comprises one component and the photosensitive layer and receiving layer are both coated on the photobase and comprise the second component. After exposure of the assembly processing fluid containing the preformed redev compound is introduced between the supercoat layer and the emulsion layer.

The formation of the photographic assembly in two components is of particular use when in-camera processing is to be carried out. When so used during exposure the photosensitive portion and the image portion may be in contact but not joined in face to face relation.

After exposure of the silver halide emulsion layer the processing liquid can be introduced between the two portions, possibly by introducing a pod between the two portions, rupturing the pod and causing the liquid to spread between the two portions which are held in close contact face to face.

However when the photographic assembly is initially in one piece there may be a stripping layer or a stripping position. This layer or position is between the silver halide emulsion layer and the receiving layer. When there is such a stripping layer or stripping position sometimes a final step in the process of the present invention is required to activate the stripping effect and to separate the portion of the photographic assembly which comprises the developed silver image from the portion which contains the dye image in the receiving layer on the photobase.

If there is a stripping layer this may be dissolved in a final wash or solution bath. An example of a suitable stripping layer is a phthalated gelatin layer.

Usually the stripping effect takes place during processing.

Alternatively there may be a stripping position, that is to say the interface between two layers is such that adhesion failure between the two layers can be caused. This adhesion failure may be caused, for example, by change of pH or temperature. The stripping position should be between the silver halide emulsion layer and the image dye layer so that the final step in the process may be to actuate adhesion failure so separating the photosensitve portion from the image portion. However it is usual for adhesion failure to occur towards the end of processing so that often no actual step to actuate stripping is required.

When the photographic assembly is initially in two portions or there is either a stripping layer or stripping position in the photographic assembly as hereinbefore defined all the silver used as the photosensitive agent can be recovered as the portion of the material containing the silver may be separated from the final image portion.

However there is considerable saving in silver even when the image portion is not separated from the portion containing the silver. In this case the final viewable image is the dye image which is viewed through the transparent photobase, there being also a silver image in the photographic material and a dye image in the layer which contains the compound of formula (1); these images are likely to be separated from the dye image in the receiving layer by a white opaque layer. In such material the amount of silver halide present in the silver halide emulsion layer can be much less than that which would be required if a viewable image were to be formed in the silver halide emulsion layer.

Thus when the assembly is developed to yield a silver image in the silver halide emulsion layer a substantial amount of redev compound is required to develop the latent silver halide, thus a comparable amount of redev compound is required to reduce the compound of formula (1) which liberates the diffusible dye which forms in the receiving layer a dye image which is considerably more dense than the silver image formed in the silver halide emulsion layer. Examples of suitable developers are: hydroquinone, N-methylaminophenol, 1-phenyl-3-pyrazolidone, 1-phenyl-4,4-dimethyl-3-pyrazolidone, ascorbic acid, aminophenols, N,N-diethyl-p-phenylenediamine, N-ethyl-N-hydroxyethyl-p-phenylenediamine and 3-methyl-N,N-diethyl-p-phenylenediamine or mixtures thereof.

When method A is used to process the assembly there is also an amplification effect, the dye image being more dense than the silver image.

The compounds of formula (1) are in general coloured compounds, thus in the process of the present invention there will, in general, be left a coloured image in the layer of the assembly which comprises the compound of formula (1). This image will be the reverse image of the dye image formed in the receiving layer.

The receiving layer of the photographic assembly used in the process of the present invention is preferably a gelatin layer which comprises a mordant (latex polymer) for the diffused dye. Other suitable (water-permeable) binder materials for mordants are casein, albumen, polyvinyl alcohol and polyvinyl pyrrolidone. The amount of latex polymer present in the binder materials may be from preferably 25 to 60% by weight of the polymer/binder (gelatin) mixture.

An example of a suitable mordant is sodium cellulose sulphate and also charged polymer particles derived from a latex of a polymer containing units of an anionically charged monomer.

Many polymer latexes are made with anionic surfactants and a proportion of these surfactant molecules may become bound to a greater of lesser degree to the polymer surface by the hydrophobe and the anionic part is then available as a further binding site for the dye. However, if too great a quantity of anionic surfactant is used and a sufficient amount of it is present for micelles to form salts with the dye this tends to prevent the dye from being effectively bound. This effect can be minimised by use of only small amounts of anionic surfactants (e.g. up to 15% surfactant) or by using nonionic surfactants.

The particle size of the latex is not critical, though to maximise the surface area and minimise optical effects it is desirable that it should be as small as can conveniently be made by use of high concentrations of initiator and surfactant or even by use of higher than atmospheric pressures during the polymerisation process. Examples of suitable particle sizes are from 0.001 to 1.0 $\mu$m.

The monomers which may be used to form the latex polymers of use in the present invention include vinyl esters, such as vinyl acetate, acrylic acid esters, methacrylic acid esters, styrene, butadiene, ethylene, vinyl and vinylidene chloride. There may also be used small amounts e.g. from 2-25 % by weight of the monomer mixture charged monomers, but preferably 2-10% by weight unless the water soluble polymer is amphoteric. Suitable charged monomers include alkali metal or ammonium salts of ethene sulphonic acid, allyl sulphonic acid, allyl oxyalkyl sulphonic acid, styrene sulphonic acid, methacryloyl oxyalkyl sulphonic acid, acrylic acid, methacrylic acid.

The initiators that may be used include persulphate salts, N,N-azo-bis cyano valeric acid, perbromate or methyl ethyl ketone/sodium formaldehyde sulphoxylate.

Suitable surfactants with which to form the latex include sodium lauryl sulphate, sodium dialkyl sulpho succinate, sodium alkyl naphthalene sulphonate, sodium alkyl benzene sulphonate, alkyl aryl poly (ethylene oxide) compounds and their sulphates and phosphates, block copoly ethylene oxide—propylene oxides compounds, alkyl aryl polyglycidol condensates.

It is preferred to make the receiving layer which contains the charged latex polymer highly permeable to allow a greater surface area to be exposed to the dye and thus the polymer latex is coated in gelatin or other water permeable binders for example, casein or polyvinyl pyrrolidone.

In the methods as hereinbefore set forth the processing is carried out in acid conditions and thus preferably in order to preserve the dye image in the receiving layer the pH of the receiving layer is raised either during the process or as a final step in the process. For example there may be present a neutralising layer in the photographic assembly through which the diffusing dye passes. Or there may be a neutralising layer located between the receiving layer and the support. However the assembly after the dye has been fixed in the receiving layer may be treated with a base to neutralise the acid or if the receiving layer and support are removed from or separated from the remainder of the photographic assembly this image portion of the assembly may be treated alone with a base.

Various embodiments of the photographic assembly of use in the present invention will now be described with reference to the accompanying drawings in which FIGS. 1 to 11 are diagrammatic cross section views showing the various layers coated on a photobase or photobases.

In FIGS. 1 to 6 the term stripping position has been used, however this may be either an interface between layers at which adhesion failure may occur or it may indicate an actual stripping layer.

In FIG. 1 there is shown a photographic material according to the present invention which can be used for X-ray film materials.

As shown in FIG. 1 the material comprises a transparent photobase 1 having coated thereon a receiving layer 2. Above this is the stripping position 3. Above the stripping position 3 is a carbon black layer 4, and above this a conventional silver halide emulsion layer 5 which also contains a compound of formula (1), (preferably an azo compound), then another carbon black layer 6 and above is a supercoat layer 7.

Thus the silver halide emulsion layer 5 is sandwiched between two carbon black layers 4 and 6 and therefore the photographic material can be handled in daylight. The material may be exposed to X-rays, preferably in a cassette, and after exposure it can be processed by method B using an aqueous acid solution of the redev compound as just described to yield a positive silver image. The silver halide layer and the two carbon black layers and the supercoat layer are then stripped off the receiving layer for recovery of the silver. The position dye image on the base can then be viewed by transmission.

Alternatively the material of FIG. 1 may be exposed and then processed using method A, that is to say a black and white silver halide development step, followed by a silver dye bleach step. In this case a negative dye image would be formed in the receiving layer.

Compounds of formula (1) are present in the assemblies shown in the remainder of the figures.

For convenience the expression "X-ray" as used in the specification is intended to cover all very short wave photographically useful actinic rays such as those emanating from an X-ray tube, radium or radioactive isotopes.

Figure 2:
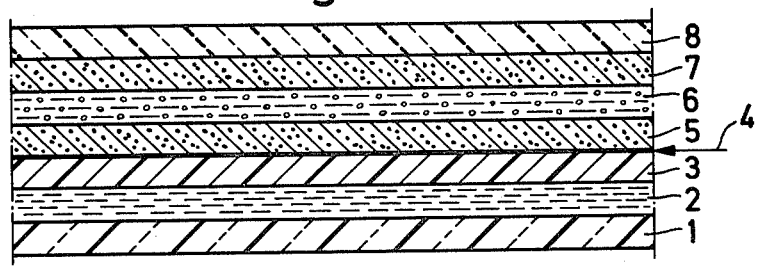

In FIG. 2 there is shown photographic material according to the present invention which can be used as X-ray material for reflection viewing. In this embodiment there is coated on a transparent film base 1 in order a receiving layer 2, a white opaque layer 3, stripping position 4, a carbon black layer 5, a conventional silver halide emulsion layer 6 which comprises a compound of formula (1), a carbon black layer 7 and a supercoat layer 8.

In this case as in the case of the material of FIG. 1 the photographic material is processed to yield either a negative image using method A or a positive image using method B. But in this material an extra white opaque layer is present. This may consist for example of baryta or titanium oxide dispersed in gelatin. In this material the white opaque layer acts as a reflective base for the dye image which is viewed by reflection through the photobase.

Figure 3:
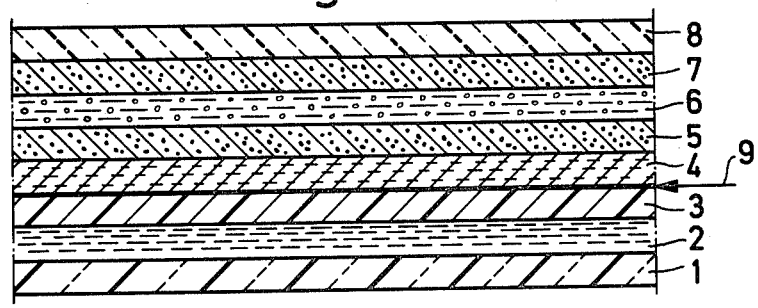
Figure 4:
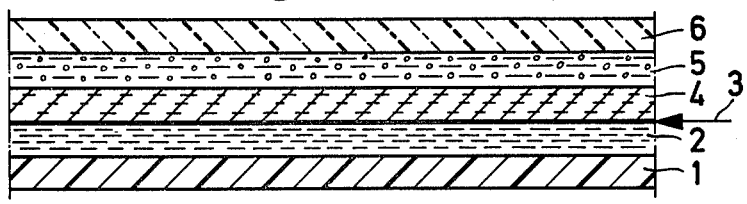

FIG. 3 shows an alternative embodiment wherein the layer which comprises the compound of formula (1) (layer 4) is separated from the silver halide emulsion layer by the carbon black layer 5. The white reflecting layer 3 comprises an alkaline substance and thus is able to act also as a neutralising layer.

Preferably the assembly of FIG. 3 is processed by ethod B. After the assembly has been exposed a preformed redev compound in aqueous acid solution is applied to the supercoat layer 8. The redev compound diffuses through layer 7 into the silver halide layer 6. There in the nonlatent image areas it diffuses down through layer 5 and into layer 4. There is reduced the compound of formula (1) and releases the diffusible dye which then diffuses through layer 3 into the receiving layer 2 to form a dye image. As the processing solution containing the redev compound diffuses through layer 3 which contains the alkaline compound its pH is raised. Thus a stable image is formed in the receiving layer 2. The diffusion of the processing solution through the assembly slowly activates the stripping effect at the stripping position between layers 3 and 4, and by the time the full image has been formed in the receiving layer the photosensitive portion of the assembly has separated from the image portion. The image may be viewed through the transparent photobase.

The main advantages of the photographic material as described with reference to FIGS. 1 to 3 is that all silver in the silver halide emulsion layer may be recovered and the film material is insensitive to daylight and thus may be handled in the unexposed state in normal daylight conditions. However, the photographic material of the present invention can also be used in a normal camera or process camera if the top carbon black layer is omitted. Such material in which there is no carbon black layer at all is shown in the accompanying FIG. 4 in which there is coated on an opaque photobase 1 in order a receiving layer 2, a stripping position 3, a compound of formula (1) (layer 4), a silver halide emulsion layer 5 and a supercoat layer 6. This material is preferably processed by method B using a preformed redev compound. After exposure the processing solution containing the preformed redev compound is applied to the supercoat layer and diffuses into the silver halide emulsion layer. In the exposed areas of the silver halide layer the redev compound develops the latent image to form a developed silver image and thus is inactivated whilst in the non-latent image areas the redev compound diffuses through the silver halide layer into the compound of formula (1) layer 4 where it reduces the azo compound in an imagewise manner and liberates the diffusible dye which diffuses to the receiving layer 2 where it is fixed to form a positive image. The stripping position 3 is then activated and the receiving layer and base are stripped off the remainder of the assembly. The dye image in the receiving layer can be viewed by reflection. In this case the material cannot be handled at any stage in daylight conditions before the silver halide layer has been stripped off.

Figure 5:
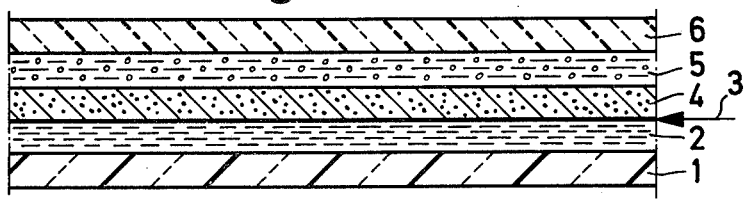

Yet another embodiment of the material of the present invention is shown in the accompanying FIG. 5. In this material there is coated on a transparent photobase 1 in order a receiving layer 2, stripping position 3, carbon black layer 4, silver halide emulsion layer 5 which also comprises a compound of formula (1), and supercoat layer 6. In this case after processing by method A or method B the material produces a final dye image which may be viewed by transmission. In the case of this material exposure must be in a camera or other light-tight exposure chamber. However, if the material is processed by method B wherein a metal foil is used which reduces the inactive redev compound and which is light opaque, this foil is placed in contact with the photographic material on the supercoat side and then the processing may be carried out under daylight conditions.

Figure 6:
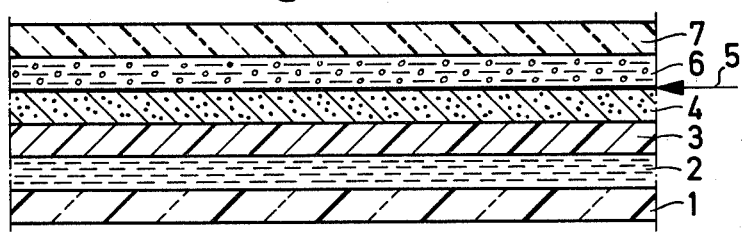

Another embodiment of the invention is shown in FIG. 6 in which there is coated on a transparent photobase 1 in order a receiving layer 2, a white opaque layer 3, carbon black layer 4, stripping position 5, silver halide emulsion layer 6 which also comprises a compound of formula (1), and supercoat layer 7. In this case also, exposure must be in a camera or light-tight exposure chamber. The silver halide emullayer 6 which also comprises an azo compound, and supercoat layer 7. The silver halide emulsion layer 6 is preferably a negative working emulsion and in which case after processing by method B there is produced a positive image which is viewed by reflection. Alternatively if a direct positive silver halide emulsion is used there is produced a negative image if processed by method B which is viewed by reflection, although of course it would be more usual in this case to employ material which would produce a positive image or to process the material so as to produce a positive image as the image is viewed by reflection unless exposure were to X-rays when it is usual to view negative images.

Figure 7:
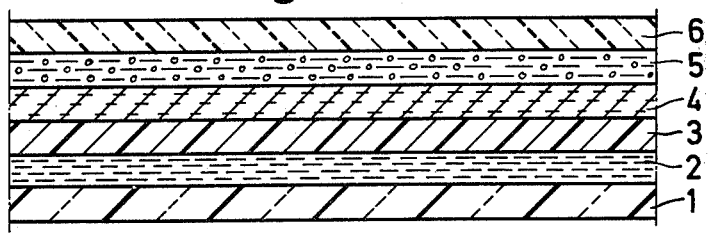
Figure 8:
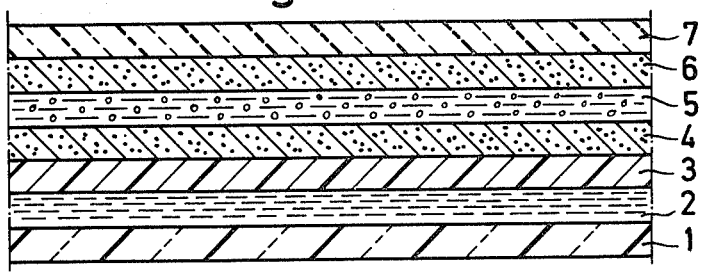

Examples of other photographic materials of use in the process of the present invention but which comprise neither a stripping layer nor a stripping position are shown in FIGS. 7 and 8.

In FIG. 7 there is coated on a photobase 1 in order a receiving layer 2, a white reflecting layer 3, a compound of formula (1) (layer 4), a silver halide emulsion layer 5 and a supercoat layer 6. Exposure must be in a camera or light-tight exposure chamber. The emulsion layer 5 or the processing conditions, i.e. using either method A or method B, may be chosen to produce a positive image or a negative image.

In FIG. 8 there is coated on a photobase 1 in order a receiving layer 2, a white reflecting layer 3, a carbon black opacifying layer 4, a silver halide emulsion layer 5 which comprises a compound of formula (1) another carbon black opacifying layer 6 and a supercoat layer 7. Exposure of this material must be to X-rays. The silver halide emulsion of this layer would preferably be a negative working emulsion and the material processed by method A so yielding a negative image to be viewed by reflection as X-ray films are by custom processed to yield negative images.

In an alternative embodiment of FIG. 8 layer 6, instead of being a carbon black opacifying layer, is a zinc powder + carbon black opacifying layer. Such material can be processed after exposure using method B to yield a dye image therein by application of an acid solution of an unreduced redev compound of the type wherein the reduced form acts as a silver halide developing agent. In this case preferably the silver halide is a direct positive emulsion so as to yield after processing a negative image.

In neither of the materials depicted in FIGS. 7 or 8 is there a stripping position or layer. This means that all the silver present initially is still present in the final image material. However it is possible to make use of a very low coating weight of silver which when the material is exposed and processed yields a very low density image, too low in fact to be of use as a final image. However the final image of the material of FIGS. 7 and 8 when processed by means of either the first method or by the second method yields dye image of very acceptable density as a final image. Thus the amount of silver used can be small as the silver is used merely as the radiation sensitive agent and not as the image-producing substance as well.

Figure 9:
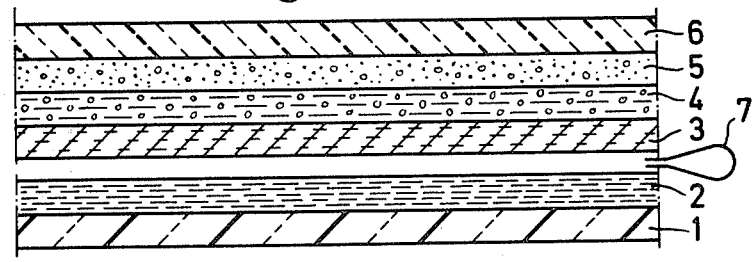

In FIG. 9 there is shown a photographic assembly of use in the present invention which comprises two separate components. The image component consists of a transparent photobase 1 on which is coated a receiving layer 2. The photographic component comprises a support layer 6 which is transparent but which is sufficiently thick and rigid to act as a photobase. On layer 6 is coated a zinc powder/gelatin binder layer 5. On layer 5 is coated a camera speed silver halide emulsion layer 4. On layer 4 is coated a layer 3 which comprises a compound of formula (1).

Between layer 2 and layer 3 there is shown a pod 7 which contains an acid solution of a metallic ion in its higher valency state but which in its lower valency state is able to act both as a silver halide developing agent and as a reducing agent for the azo compound.

The assembly of FIG. 9 is of use in a self-processing camera of the type known per se. In operation the assembly preferably with the pod 7 already in position between the two components of the assembly is imagewise exposed through the supercoat layer 6. After exposure the assembly is processed by method B by leading it through a pair of driven rollers which rupture the pod 7 and cause the processing fluid contained therein to spread evenly between the two components and it also brings the two components into very close contact. The unreduced metallic ions in the acid solution from the ruptured pod then diffuse into both components but are not able to either develop the latent image in the silver halide or to reduce the compound of formula(1) until some of the compound has reached layer 5 and there the ions are reduced to the active form. The reduced ions then diffuse through the assembly. In layer 4 they develop the latent image areas and are deactivated. In the non-latent image areas they continue to diffuse down into layer 3 where they reduce the compound of formula (1) in an imagewise manner and liberate the diffusible dye which in its turn diffuses down through the thin layer of solution between layers 2 and 3 and to layer 2, the receiving layer, where it is fixed to form a dye image.

In this case as a camera speed emulsion is used the emulsion is preferably a negative emulsion. Thus a positive dye image will be formed as processing method B has been employed.

Figure 10:
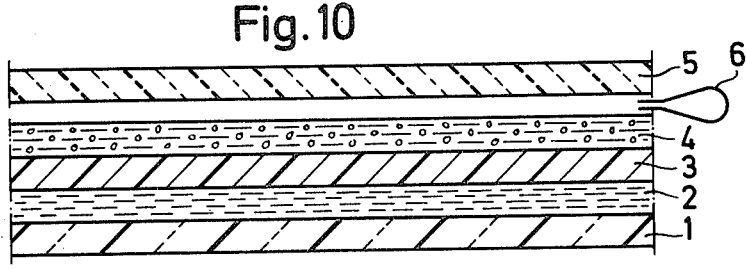

In FIG. 10 there is shown a photographic assembly of use in the present invention which comprises two separate components. The first component consists only of a separate support 5. The other component comprises a transparent photobase 1 having coated thereon in order a receiving layer 2, a white reflecting layer 3, and a silver halide emulsion layer 4 which comprises a compound of formula (1). Between the support layer 5 and the silver halide layer 4 is shown a pod 6 which contains a preformed (active) redev compound.

The assembly of FIG. 10 is of use in a self-processing camera of the type known per se. In operation the assembly with the supercoat layer 5 in close contact with the silver halide emulsion layer 4 is imagewise exposed in a camera. Preferably the pod 6 is present in the assembly with its outlet between two edges of the support and silver halide emulsion layers but is so positioned that close optical contact between these two layers is not impaired.

After exposure the assembly is led through a pair of driven rollers which rupture the pod 6 and cause the redev processing fluid contained therein to spread evenly between the supercoat layer 5 and the silver halide emulsion layer 4. The preformed redev compound then diffuses into the silver halide layer and develops the latent image therein in the latent image areas. In the non-latent image areas it reduces the compound of formula (1) and liberates a diffusible dye which diffuses imagewise through the white reflecting layer 3 to the receiving layer 2 where it forms a positive image. The image is viewed by reflection through the transparent photobase 1.

Figure 11:
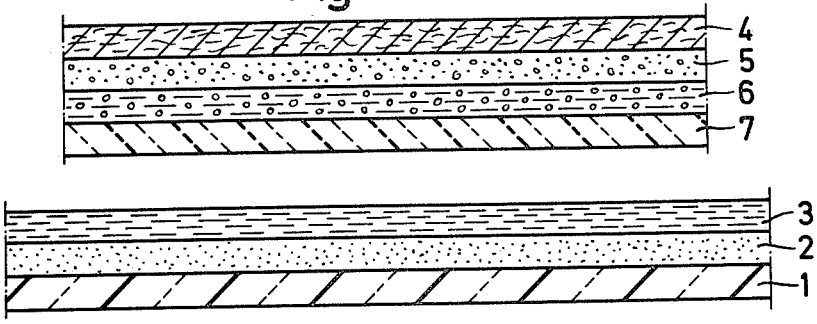

In FIG. 11 there is shown another photographic assembly of use in the present invention which comprises two separate components. The lower component comprises a transparent photobase 1, a neutralising layer 2, a receiving layer 3. The upper component comprises coated on a paper base 4 a zinc powder+binder layer 5, a silver halide emulsion layer 6 which comprises a compound of formula (1) and a protective layer 7. The lower component may be part of a long web of material.

In operation after the upper component has been imagewise exposed in a camera through the supercoat layer 7 the upper component is placed juxtaposed the lower component, layer 7 facing layer 3. Then an inactive form of redev compound is spread either as a dispersion or as a solution on either layer 7 or layer 3 and the two components are brought together and held in close contact.

The inactive redev compound then diffuses through layers 7 and 6 into layer 5 where it is converted to the active form. The active form then diffuses into layer 6 where in the latent image areas it develops the latent silver image whilst in the non-latent image areas it reduces the compound of formula (1) and liberates the diffusible dye which diffuses imagewise through the protective layer 7 and enters the receiving layer 3 where it is fixed to form a positive image. The neutralising layer 2 acts to neutralise the acid processing solution used. The upper component can then be removed and the silver recovered therefrom. The image can be viewed through the transparent base. In practice if the lower component is part of a web a series of dye images will be present along the length of the web if the process has been repeated using a series of exposed upper components.

Figure 12:
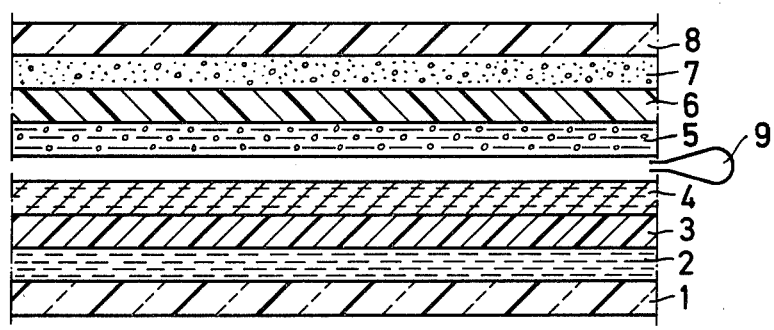

In FIG. 12 is shown another photographic assembly of use in the present invention which comprises two separate components. The lower component comprises a transparent support 1, a receiving layer 2, a white reflecting layer 3, and a layer 4 containing the dye releasing compound of formula (1). The upper component comprises a transparent base 8, and coated thereon a layer containing zinc powder 7, an interlayer 6 and a silver halide emulsion layer 5. Between the two components is shown a pod 9 which contains the inactive form of a redev compound in acid solution.

The assembly of FIG. 12 is of use in a self-processing camera. In operation the two halves of the assembly are held in close contact, or with a suitable spacer in between, and the silver halide emulsion layer 5 is exposed in a camera through the zinc layer 7. Processing is initiated as for the assembly of FIG. 10, releasing the redev compound from the pod 9. This diffuses to the zinc layer 7 were it is reduced to the active form of the redev compound, which then diffuses to the silver halide emulsion layer 5 where it develops silver in latent image areas and is rendered inactive. In non latent image areas the active form diffuses further to the layer 4 containing the compound of formula (1), liberating the diffusible dye, which diffuses to the receiving layer 2 and is mordanted to form a positive dye image.

Alternatively exposure to light may be before the two portions of the assembly are brought into contact, in which case the redev compound need not be spread by rupture of a pod.

An example of a suitable white reflecting layer for use in the material of FIGS. 2, 3, 6–8 and 10 is as follows

| | |
|---|---|
| Titanium dioxide (mean particle size 1.5μ) | 15 g |
| Gelatin (4% aqueous solution) | 50 ml |
| Sodium dodecyl sulphate (28% aqueous solution) | 0.3 ml |
| Aryl alkyl polyethylene oxide condensate (6% solution in 50/50 ethanol/water) | 3.0 ml | dispersed using a homogeniser or ultrasonic mixer coated to give a layer containing 27 g.m$^{-2}$ TiO$_2$.

An example of a suitable carbon black layer for use in the material of FIGS. 1–3 and 5–8 is as follows:

| | |
|---|---|
| Gelatin | 3 g |
| Water | 40 ml |
| Carbon black dispersion | 5 ml |
| Wetting agent (alkyl aryl polyglycidol condensate, 5% aqueous solution) | 2.5 ml | mixed gently for two minutes coated to give a layer containing 2.7 g.m$^{-2}$ C.

There may be present in the photographic material of the present invention yet other layers, for example a neutralising layer, a timing layer, a mordant layer or a layer to control the swelling of the gelatin layers. Preferably any of the above layers, if present, are located between the supercoat layer and the silver halide emulsion layer or between the dye layer and the photobase so as not to prolong nor interfere with the diffusion path of the diffusible dye to the receiving layer.

The preferred binder for all layers is gelatin. However so-called gelatin extenders may be present, for example those derived for synthetic colloid latexes especially acrylic latexes. Other natural or synthetic binders may be used either alone or in admixture with the gelatin, for example albumin, casein, polyvinyl alcohol and polyvinylpyrolidine.

The halide content and ratio of the silver halide present in the silver halide layer depends on how the material is to be used but all the usual pure bromide, chlorobromide, iodobromide and chlorobromoiodide silver halides are of use in the photographic material of use in the process of the present invention. There may also be present in the silver halide emulsion layer any of the usual addenda present in silver halide emulsion layers such as sulphur and gold sensitsers, emulsion stabilizers, sensitising dyes, hardening agents, wetting agents and antifoggants.

The photobase in support may be of any of the usual bases used for photographic materials, for example if the base is transparent it may be composed of cellulose triacetate, cellulose acetatebutyrate, oriented and subbed polystyrene, or polycarbonate or polyester such as polyethylene terephthalate. If the base is opaque it may be of any of the above listed film base materials which has been pigmented for example with magnesium carbonate or titanium dioxide to render its coated surface reflecting or it may be a paper base having a baryta coating thereon or polyethylene coated paper base. Alternatively it may be 'voided' polyester base, i.e. polyester base containing many voids which render it opaque.

The following Manufacturing instructions and Examples will serve to illustrate the invention. Parts and percentages are by weight.

Manufacturing Instruction

In a 2 liter reaction ves, de-oxygenated water 600 ml is heated to 50° C. and 0.8 g of initiator is added. After a few minutes, 400 g of the monomers, and 20 g of surfactant are added and the vessel is stirred continuously for four hours. The completed latex was then decanted.

Surfactants which can be used in the preparation of the polymer latexes are for example those of formula

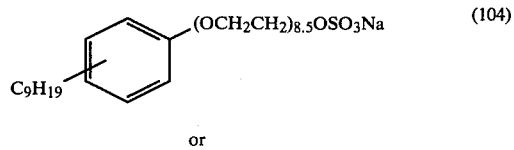

(104)

or

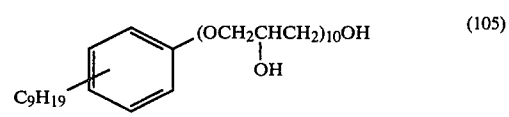

(105)

| No. of polymer | Monomer A (parts) | Monomer B (parts) | Initiator | Surfactant (parts) |
|---|---|---|---|---|
| 1 | Methyl acrylate (90) | 2-ethyl hexyl acrylate (10) | persulphate/ meta- bisulphite 3/1 | [104] (7) |
| 2 | Styrene (50) | butyl acrylate (50) | persulphate/ meta- bisulphite 3/1 | [104] (7) |
| 3 | Styrene (50) | butyl acrylate (50) | persulphate/ meta- bisulphite 3/1 | [105] (5) |
| 4 | Styrene (50) | methyl acrylate (50) | persulphate/ meta- bisulphite 3/1 | [105] (5) |
| 5 | Styrene (47.5) | butyl acrylate (47.5) acrylic acid (5) | persulphate/ meta- bisulphite 3/1 | [104] (7) |

| No. of polymer | Monomer A (parts) | Monomer B (+ C) (parts) | Initiator | Surfactant (parts) |
|---|---|---|---|---|
| 6 | Methyl acrylate (86) | 2 Ethyl hexyl acrylate (9) Na ethene sulphonate (5) | persulphate/ meta- bisulphite 3/1 | [104] (7) |
| 7 | Methyl acrylate (86) | 2 Ethyl hexyl acrylate (9) + Na allyl sulphonate (5) | persulphate/ meta- bisulphite 3/1 | [104] (7) |
| 8 | Styrene (47.5) | Butyl acrylate (47.5) + oxypropane sulphonate (5) | persulphate/ meta- bisulphite 3/1 | [105] (10) |
| 9 | Butyl acrylate (95) | Na methacryloyl oxypropane sulphonate (5) | persulphate/ meta- bisulphite 3/1 | [105] (10) |

| No. of polymer | Monomer A (parts) | Monomer B (parts) | Initiator | Surfactant (parts) |
|---|---|---|---|---|
| 10 | Styrene (50) | Butyl acrylate (50) | N,N'—azo-bis cyanovaleric acid | [104] (5) |

-continued

| | | | | |
|---|---|---|---|---|
| 11 | Styrene (50) | Butyl acrylate (50) | butanone peroxide/Na formaldehyde sulphoxylate | [104] (5) |
| 12 | N—isopropyl acrylamide (80) | Methacryloyloxy propane sulphonate (20) | persulphate bisulphite | None |
| 13 | Styrene (50) | Butyl acrylate (50) | persulphate bisulphite | [104] (5) |
| 14 | Styrene (75) | Isoprene (25) | persulphate bisulphite | Na lauryl sulphate (7) |
| 15 | Vinyl acetate (85) | ethylene (15) | persulphate bisulphite | Na dioctyl sulpho succinate (10) |
| 16 | Styrene (50) | Butyl acrylate (50) | persulphate bisulphite | 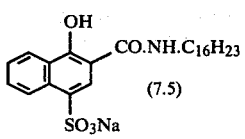 (7.5) |

EXAMPLE 1

Example of method A using the assembly of FIG. 7. A photosensitive material was prepared by coating sequentially onto a 1. 0.1 mm thick transparent colourless photobase the following layers:
2. A receiving layer containing as mordant the charged copolymer (2) (1.5 g solids $m^{-2}$) and gelatin (4.0 g $m^{-2}$). Instead of copolymer (2) copolymers (1) and (3) to (16) can be used. The same good results are obtained.
3. A reflecting layer containing titanium dioxide (23 g $m^{-2}$) and gelatin (3.0 g $m^{-2}$).
4. An azo compound layer containing the dye releasing compound of formula (11) (0.1 g $m^{-2}$) in gelatin (3.0 g $m^{-2}$).
5. A silver bromide emulsion layer containing 1.5 g $m^{-2}$ silver in gelatin (2.0 g $m^{-2}$).
6. A supercoat layer containing gelatin (10 g $m^{-2}$).

The above photosensitive material was exposed to light behind a grey wedge and then processed in the dark at 20° C. using the following baths in sequence:

| | | Time |
|---|---|---|
| 1. A 1-phenyl-3-pyrazolidone-hydroquinone developing solution | | 3 mins |
| 2. Silver dye-bleach solution | | |
| 2,3-dimethylquinoxaline | 0.365 g | |
| sulphuric acid (0.61M) | 163 ml | |
| potassium iodide | 1.2 g | 3 mins |
| Glacial acetic acid | 0.4 ml | |
| 2-ethoxyethanol | 12 ml | |
| distilled water | 7.6 ml | |
| 3. Water wash | | 1 min |

After processing a negative magenta image of the wedge was obtained in the receiving layer which could be viewed through the base.

Instead of 2,3-dimethylquinoxaline in the silver dye bleach solution the following 1,4-diazines can be used: 2,3-dipyridylquinoxaline, 2,3-dimethyl-6-carboxyquinoxaline, 2-carboxy-3-benzyl-quinoxaline, 2-acetyl-3-phenyl-quinoxaline, 2-methyl-3-benzoyl-quinoxaline, quinoxaline, pyrazine, 2,3-dimethyl-6-sulfomethyl-quinoxaline, 2-methyl-3-acetyl-6-sulfo-quinoxaline or 2-methyl-3-acetyl-quinoxaline.

EXAMPLE 2

Example of Method B using the assembly of FIG. 7 A photosensitive material was prepared by coating sequentially onto a 1. Transparent colourless photobase (0.1 mm) the following layers:
2. A receiving layer as in Example 1
3. A reflecting layer as layer 3 in Example 1
4. An azo compound layer as layer 4 in Example 1
5. A silver bromide emulsion layer as layer 5 in Example 1
6. A supercoat layer as layer 6 in Example 1

After exposure to light behind a grey wedge the material was processed in the dark at 20° in the following manner:

1. The exposed material was soaked for 10 seconds in a solution containing:
pyrazine 0.25 g
sulphuric acid (0.2 M) 100 ml
2. The supercoat of the soaked material was then coated with zinc foil for 10 seconds, and then peeled apart.
3. The processed material was washed in water for 1 minute.

After processing a positive magenta image of the wedge was obtained in the receiving layer which could be viewed through the base.

EXAMPLE 3

Example of Method A using the assembly of FIG. 7 A photosensitive material was prepared by coating sequentially onto a 1. 0.1 mm thick transparent colourless photobase the following layers:
2. A receiving layer containing as mordant a charged copolymer (2) (1.5 g solids $m^{-2}$) and gelatin (4.0 g $m^{-2}$)
3. A reflecting layer containing titanium dioxide (23 g $m^{-2}$) and gelatin (3.0 g $m^{-2}$)
4. An azo compound layer containing the dye releasing compound of formula (59) (0.16 g $m^{-2}$) in gelatin (4.0 g $m^{-2}$)
5. A silver bromide emulsion layer containing 1.5 g $m^{-2}$ silver in gelatin (2.0 g $m^{-2}$)
6. A supercoat layer containing gelatin (10 g $m^{-2}$)

The above photosensitive material was exposed to light behind a grey wedge and then processed in the dark at 20° C. using the following baths in sequence

| | Time |
|---|---|
| 1. A 1-phenyl-3-pyrazolidinone-hydroquinone developing solution | 3 mins |
| 2. Silver dye-bleach solution | |
|    2,3-dimethylquinoxaline   0.36 g | |
|    sulphuric acid (0.61M)   163 ml | |
|    potassium iodide   1.2 g | 3 mins |
|    glacial acetic acid   0.4 ml | |
|    2-ethoxyethanol   12 ml | |
|    distilled water   7.6 ml | |
| 3. Water wash | 1 min |

After processing a negative cyan image of the wedge was obtained in the receiving layer which could be viewed through the base.

EXAMPLE 4

Example of Method B using the assembly of FIG. 7 A photosensitive material was prepared by coating sequentially onto a 1. Transparent colourless photobase (0.1 mm thick) the following layers:
2. A receiving layer as in Example 3
3. A reflecting layer as layer 3 in Example 3
4. An azo compound layer as layer 4 in Example 3
5. A silver bromide emulsion layer as layer 5 in Example 3
6. A supercoat layer as layer 6 in Example 3

After exposure to light behind a grey wedge the material was processed in the dark at 20° C. in the following manner:

1. The exposed material was soaked for 10 seconds in a solution containing:
pyrazine 0.25 g
sulphuric acid (0.2 M) 100 ml
2. The supercoat of the soaked material was then contacted with zinc foil for 10 seconds, and then peeled apart.
3. The processed material was washed in water for 1 minute.

After processing a positive cyan image of the wedge was obtained in the receiving layer which could be viewed through the base.

EXAMPLE 5

Example of Method B using the assembly of FIG. 12 Layers 1 to 4 of the assembly of FIG. 12 are prepared by coating sequentially onto a 1. 0.1 mm thick transparent colourless support base the following layers:
2. A receiving layer as layer 2 of Example 1
3. A reflecting layer as layer 3 of Example 1
4. A layer containing the dye releasing compound of Formula (68) (0.1 g. m$^{-2}$) in gelatin (1.0 g. m$^{-2}$).

The photosensitive portion of the assembly of FIG. 12 is prepared by coating sequentially onto:a 8. 0.1 mm thick transparent colourless support base the following layers:

7. A zinc layer (0.9 g. m$^{-2}$) having an average particle size of 3 microns
6. A gelatin interlayer having a swollen thickness of 30 microns
5. A silver bromide emulsion layer (1.2 g. m$^{-2}$).

The photosensitive portion of the assembly was exposed to light through a silver step wedge and then the two halves of the assembly were contacted by passing between rollers, after introducing a processing solution which has the following composition:

| 1N HCl | 50 ml |
|---|---|
| water | 50 ml |
| Pyrazine | 0.5 g |
| thickening agent (Natrosol 250 HH) | 0.75 g. |

A positive blue image of the wedge is received in the receiving layer after this has been separated and neutralised with aqueous sodium hydroxide solution.

An oil dispersion was made as follows:

| Compound of formula (68) | 0.1 g |
|---|---|
| Tricresyl phosphate | 0.4 ml |
| Dichloromethane | 1.6 ml |

The dichloromethane was evaporated off and the residue mixed with

| 6% gelatin solution | 13 ml |
|---|---|
| water | 5 ml |

Treated ultrasonically for 5 minutes. The coating solution contains:

| the above dispersion | 3 ml |
|---|---|
| 6% gelatin solution | 3 ml |
| hardener (formaldehyde) | 1 ml |
| saponin (wetting agent) | 0.5 ml |
| water | 2.5 ml. |

EXAMPLE 6

Example of Method B using the assembly of FIG. 12 Layers 1 to 4 of the assembly of FIG. 12 are prepared by coating sequentially onto a 1. 0.1 mm thick transparent colourless support base the following layers:
2. The receiving layer as layer 2 of Example 1
3. The reflecting layer as layer 3 of Example 1
4. A layer containing the dye releasing compound of formula (85) (0.15 g. m$^{-2}$) in gelatin (2.5 g. m$^{-2}$)

The photosensitive portion of the assembly was prepared as in Example 5. On exposure and processing as in Example 5 a magenta image is obtained in the receiving layer.

The dispersion was made as follows:

Compound of formula (85) (0.1 g) in chloroform was slowly added to a warm 5% gelatin solution (50 ml) under a sonic probe, allowing the chloroform to evaporate off.

The same results can be obtained by using the other compounds (dyestuffs) hereinbefore mentioned.

We claim:

1. Photographic material which comprises in order optionally a supercoat layer, at least one silver halide emulsion layer, a dye mordant layer and a support base, there being associated with the silver halide emulsion layer a compound of the general formula $$D-N=CR_{17}-BAL \text{ or} \tag{60}$$

an amino compound of formula $$D-N-CR_{17}R_{19}-BAL, \quad (61)$$
$$\overset{|}{R_{18}}$$

wherein D represents a diffusible dye residue, BAL represents a ballasting group and $R_{17}$, $R_{18}$ and $R_{19}$ each represent hydrogen or alkyl with 1 to 3 carbon atoms.

2. Photographic material according to claim 1 which comprises a layer which contains a metal which in the electrochemical series is above silver and up to an including lanthanum, which is able to active a non-active redev compound.

3. Photographic material according to claim 2 wherein the layer which comprises the metal which in the electrochemical series is above silver and up to and including lanthanum is on the side of the silver halide emulsion layer remote from the dye mordant layer.

4. Photographic material according to claim 1 wherein there is present between the silver halide emulsion layer and the dye mordant layer a light opaque layer.

5. Photographic material according to claim 1 wherein there is present between the silver halide emulsion layer and the dye mordant layer a white reflecting layer.

6. Photographic material according to claim 1 wherein there is present in order a supercoat layer, optionally at least one interlayer, a silver halide emulsion layer which comprises the compound of formula (1) a light opaque layer, a white reflecting layer, a dye mordant layer and a support base.

7. Photographic material according to claim 1 wherein there is present between the supercoat layer and the silver halide emulsion layer a light opaque layer.

8. Photographic material according to claim 1 wherein there is present in the material between silver halide emulsion layer and the dye mordant layer a stripping position or stripping layer.

9. Photographic material according to claim 1 wherein the dye mordant layer comprises as the mordant a polymer which comprises units of an anionically charged monomer.

10. Photographic material which comprises in order optionally a supercoat layer, at least one silver halide emulsion layer, a dye mordant layer and a support, there being associated with the silver halide emulsion layer a compound of the formula $$D-N=N-BAL,$$

wherein
D represents a diffusible dye selected from the group consisting of azophenazine, azo-oxazine, azo-thiazine, azo-acridine, azo-pyrylium, azo- and hydrazoanthraquinone, azo-phthalocyanine, azopyrazolone, azo-hydroxypyridone and azoxy compounds and BAL is a ballasting group.

* * * * *